US012183469B1

(12) United States Patent
Warnick et al.

(10) Patent No.: US 12,183,469 B1
(45) Date of Patent: Dec. 31, 2024

(54) METHOD AND SYSTEM FOR ACCURATELY TRACKING AND INFORMING OF HEALTH AND SAFETY FOR GROUP SETTINGS

(71) Applicant: UIPCO, LLC, San Antonio, TX (US)

(72) Inventors: Mark Paxman Warnick, San Antonio, TX (US); Will Kerns Maney, Jr., San Antonio, TX (US); Phillip E. Marks, San Antonio, TX (US); David Jason Anderson James, San Antonio, TX (US); Elena Marie Carrasco, Converse, TX (US); Quian Antony Jones, San Antonio, TX (US); Sumita T. Jonak, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 326 days.

(21) Appl. No.: 17/164,332

(22) Filed: Feb. 1, 2021

Related U.S. Application Data

(60) Provisional application No. 63/107,008, filed on Oct. 29, 2020.

(51) Int. Cl.
*G16H 50/80* (2018.01)
*A61B 5/00* (2006.01)
*A61B 5/1455* (2006.01)
(Continued)

(52) U.S. Cl.
CPC ........... *G16H 50/80* (2018.01); *A61B 5/7275* (2013.01); *G06Q 10/0635* (2013.01);
(Continued)

(58) Field of Classification Search
CPC ........ G16H 50/30; G16H 50/80; G16H 40/67; G16H 15/00; H04W 4/029; G06V 40/168;
(Continued)

(56) References Cited

U.S. PATENT DOCUMENTS 11,504,011 B1 * 11/2022 Jain .......................... G06N 5/04
2015/0213225 A1 * 7/2015 Amarasingham ...... G16H 50/30
705/2
(Continued)

FOREIGN PATENT DOCUMENTS

WO WO-2020061562 A1 * 3/2020 ........... A61B 5/0022

OTHER PUBLICATIONS

S. M. Alshammari and A. R. Mikler, "Modeling Disease Spread at Global Mass Gatherings: Hajj as a Case Study," 2015 International Conference on Healthcare Informatics, 2015, pp. 574-577, doi: 10.1109/ICHI.2015.107. (Year: 2015).*
(Continued)

*Primary Examiner* — Evangeline Barr
*Assistant Examiner* — Patricia K. Edouard
(74) *Attorney, Agent, or Firm* — Plumsea Law Group, LLC

(57) ABSTRACT

A user score of a test for assessing a risk of a user of having or developing a contagious illness may be obtained, for each user of a plurality of users entering in a group setting. A group score based on the user scores associated with the plurality of users in the group setting may be generated. The group score indicating a group risk of a presence or development of the contagious illness in the group setting may be communicated for display. Group scores associated with a plurality of group settings may be obtained and communicated for display. A message may be communicated to a mobile user device indicating a group setting as a current high risk group setting, being associated with a score that is outside a limit set by a threshold value and with a location in proximity to a current location of the mobile user device.

14 Claims, 16 Drawing Sheets

(51) Int. Cl.
*G06Q 10/0635* (2023.01)
*G06Q 50/26* (2024.01)
*G06V 40/16* (2022.01)
*G07C 9/00* (2020.01)
*G10L 25/66* (2013.01)
*G16H 15/00* (2018.01)
*G16H 40/67* (2018.01)
*G16H 50/30* (2018.01)
*H04W 4/029* (2018.01)

(52) U.S. Cl.
CPC ......... *G06Q 50/265* (2013.01); *G06V 40/168* (2022.01); *G07C 9/00* (2013.01); *G10L 25/66* (2013.01); *G16H 15/00* (2018.01); *G16H 40/67* (2018.01); *G16H 50/30* (2018.01); *H04W 4/029* (2018.02); *A61B 5/14551* (2013.01)

(58) Field of Classification Search
CPC .............. A61B 5/7275; A61B 5/14551; G06Q 10/0635; G06Q 50/265; G07C 9/00; G10L 25/66
See application file for complete search history.

(56) References Cited

U.S. PATENT DOCUMENTS

| | | | |
|---|---|---|---|
| 2017/0024531 A1* | 1/2017 | Malaviya | G16H 50/30 |
| 2017/0286622 A1* | 10/2017 | Cox | G16H 50/30 |
| 2018/0296092 A1* | 10/2018 | Hassan | G16H 50/20 |
| 2020/0090089 A1* | 3/2020 | Aston | G06Q 10/0635 |
| 2020/0372743 A1* | 11/2020 | Miller | G07C 9/257 |
| 2021/0012869 A1* | 1/2021 | Kotlarz | G16H 15/00 |
| 2021/0327595 A1* | 10/2021 | Abdallah | A61B 5/02055 |
| 2022/0028562 A1* | 1/2022 | Klasson | G06F 40/30 |
| 2022/0277604 A1* | 9/2022 | Klein | G06Q 50/265 |

OTHER PUBLICATIONS

Sandeep K. Sood, Isha Mahajan, Wearable IoT sensor based healthcare system for identifying and controlling chikungunya virus, Computers in Industry, vol. 91, 2017, pp. 33-44, ISSN 0166-3615, https://doi.org/10.1016/j.compind.2017.05.006. (Year: 2016).*

* cited by examiner

| GROUP SETTING | NAME | LOCATION | GROUP SCORE |
|---|---|---|---|
| COFFEE SHOP | KARIN'S KAFE | ADDRESS 1/ GEOLOC 1 | 9/10 |

FIG. 7

| GROUP SETTING | NAME | LOCATION | GROUP SCORE |
|---|---|---|---|
| COMPANY/ BUSINESS | JOHN INC | ADDRESS 2/ GEOLOC 2 | 8/10 |

FIG. 8

GENERATE AN AVERAGE GROUP SCORE ASSOCIATED WITH THE GROUP SETTING BASED ON A PLURALITY OF SAMPLE GROUP SCORES OBTAINED OVER A PERIOD OF TIME, THE AVERAGE GROUP SCORE INDICATING AN AVERAGE GROUP RISK OF THE PRESENCE OR DEVELOPMENT OF THE CONTAGIOUS ILLNESS IN THE GROUP SETTING

FIG. 9

IDENTIFY A PEAK VALUE OF THE GROUP SCORE ASSOCIATED WITH THE GROUP SETTING OVER A PERIOD OF TIME

FIG. 10

| GROUP SETTING | GROUP SCORE |
| --- | --- |
| RESTAURANT 1 | 95 / 100 SAFE |
| RESTAURANT 2 | 92 / 100 SAFE |
| RESTAURANT 3 | 69 / 100 |
| COFFEE SHOP 1 | 85 / 100 SAFE |
| COFFEE SHOP 2 | 82 / 100 SAFE |
| COFFEE SHOP 3 | 60 / 100 |
| HOSPITAL 1 | 84 / 100 SAFE |
| HOSPITAL 2 | 55 / 100 |
| HOSPITAL 3 | 54 / 100 |
| PARK CONCERT 1 | 98 / 100 SAFE |
| PARK CONCERT 2 | 95 / 100 SAFE |
| PARK CONCERT 3 | 92 / 100 SAFE |

FIG. 22

PROVIDE THE PLURALITY OF GROUP SCORES ASSOCIATED WITH A PLURALITY OF LOCATIONS ON AN INTERACTIVE MAP OF A WEB MAPPING SERVICE AND APPLICATION

FIG. 23

METHOD AND SYSTEM FOR ACCURATELY TRACKING AND INFORMING OF HEALTH AND SAFETY FOR GROUP SETTINGS

CROSS-REFERENCE TO RELATED APPLICATION(S)

This application claims the benefit of U.S. Provisional Patent Application No. 63/107,008, filed Oct. 29, 2020, and titled "Method and System for Accurately Tracking and Informing of Health and Safety for Group Settings", the disclosure of which application is incorporated by reference herein in its entirety.

TECHNICAL FIELD

The present disclosure generally relates to methods and systems for maintaining health and safety, and in particular, to methods and systems for accurately tracking and informing of health and safety with respect to contagious illnesses for group settings.

BACKGROUND

Under occupational safety and health laws, employers and other organizations have duties to maintain safe operating environments. Those duties may include taking reasonable measures to prevent the spread of disease. For example, in order to prevent the outbreak of contagious diseases, organizations should take basic measures, such as making tissues and antibacterial soap available. Encouraging hand washing, disinfecting, offering flu shots, and urging people to get immunizations are also good practices. Of course, other group settings may have the same or similar concerns and needs.

One notable concern is a recent virus that was designated as severe acute respiratory syndrome coronavirus 2 (SARS-CoV-2) defined to be the causal agent of Coronavirus Disease 2019 (COVID-19). Despite attempts to contain the disease, the virus has spread globally and COVID-19 was declared a pandemic by the World Health Organization (WHO) in March 2020.

There is a need in the art for methods and systems for maintaining health and safety with respect to contagious illnesses for group settings that address the problems discussed above, as well as related issues.

SUMMARY

Various methods and systems for accurately tracking and informing of health and safety with respect to contagious illnesses for group settings are described herein.

In one aspect, a user score of a test for assessing a risk of a user of having or developing a contagious illness may be obtained, for each user of a plurality of users entering in a group setting. A group score based on the user scores associated with the plurality of users in the group setting may be generated. The group score may indicate a group risk of a presence or development of the contagious illness in the group setting. The group score indicating the group risk of the presence or development of the contagious illness in the group setting may be communicated for display. In some embodiments, the user score may be obtained based on a reading of a user device of the user at an access control system for entry in the group setting.

In another aspect, a score indicating a group risk of a presence or development of a contagious illness in a group setting may be obtained, for each group setting of a plurality of group settings. The scores associated with the plurality of group settings may be communicated for display. At least a subset of the group settings may be grouped according to a group setting type, where locations or names of the group settings of the grouped subset of the same group setting type are communicated for display in association with the group scores.

In yet another aspect, location-based techniques may be utilized for accurately tracking and informing of health and safety for group settings for a mobile user device. A system may include a server configured to connect in a network and the mobile user device which is configured to connect in a mobile network for communications. The server may be configured to obtain a score indicating a group risk of a presence or development of a contagious illness in a group setting and store the score in association with a location of the group setting, for each group setting of a plurality of group settings. The server may be further configured to obtain a current location of the mobile user device connected in the mobile network. The server may be further configured to communicate to the mobile user device a message indicating one of the plurality of group settings as a current high risk group setting that is associated with a score that is outside a limit set by a threshold value and with a location in proximity to the current location of the mobile user device.

Other techniques, mechanisms, features, and advantages of the disclosure will be, or will become, apparent to one of ordinary skill in the art upon examination of the following figures and detailed description. It is intended that all such additional techniques, mechanisms, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 7 is an illustrative example of a first display item associated with a first group score indicating a first group risk of a presence or development of a contagious illness in a first group setting;

FIG. 8 is an illustrative example of a second display item associated with a second group score indicating a second group risk of a presence or development of a contagious illness in a second group setting;

FIG. 9 is a flowchart for describing a method for use in accurately tracking and informing of health and safety for a group setting according to some embodiments, which may be performed by or with use of the access control system of FIGS. 1-3 and together with the methods described in relation to FIGS. 5 and 6;

FIG. 10 is a flowchart for describing a method for use in accurately tracking and informing of health and safety for a group setting according to some embodiments, which may be performed by or with use of the access control system of FIGS. 1-3 and together with the methods shown and described in relation to FIGS. 5 and 6;

FIG. 22 is an illustrative example of a display having a plurality of display items indicating a plurality of group scores respectively associated with a plurality of group settings, in grouped subsets of the same group subset type;

FIG. 23 is a flowchart for describing a method for use in accurately tracking and informing of health and safety for a plurality of group settings according to some embodiments, which may be performed by a server in communication with systems associated with the plurality of group settings and together with the method shown and described in relation to FIG. 20, for displaying the group scores or indicators thereof on an interactive map;

DESCRIPTION OF EMBODIMENTS

Figure 1:
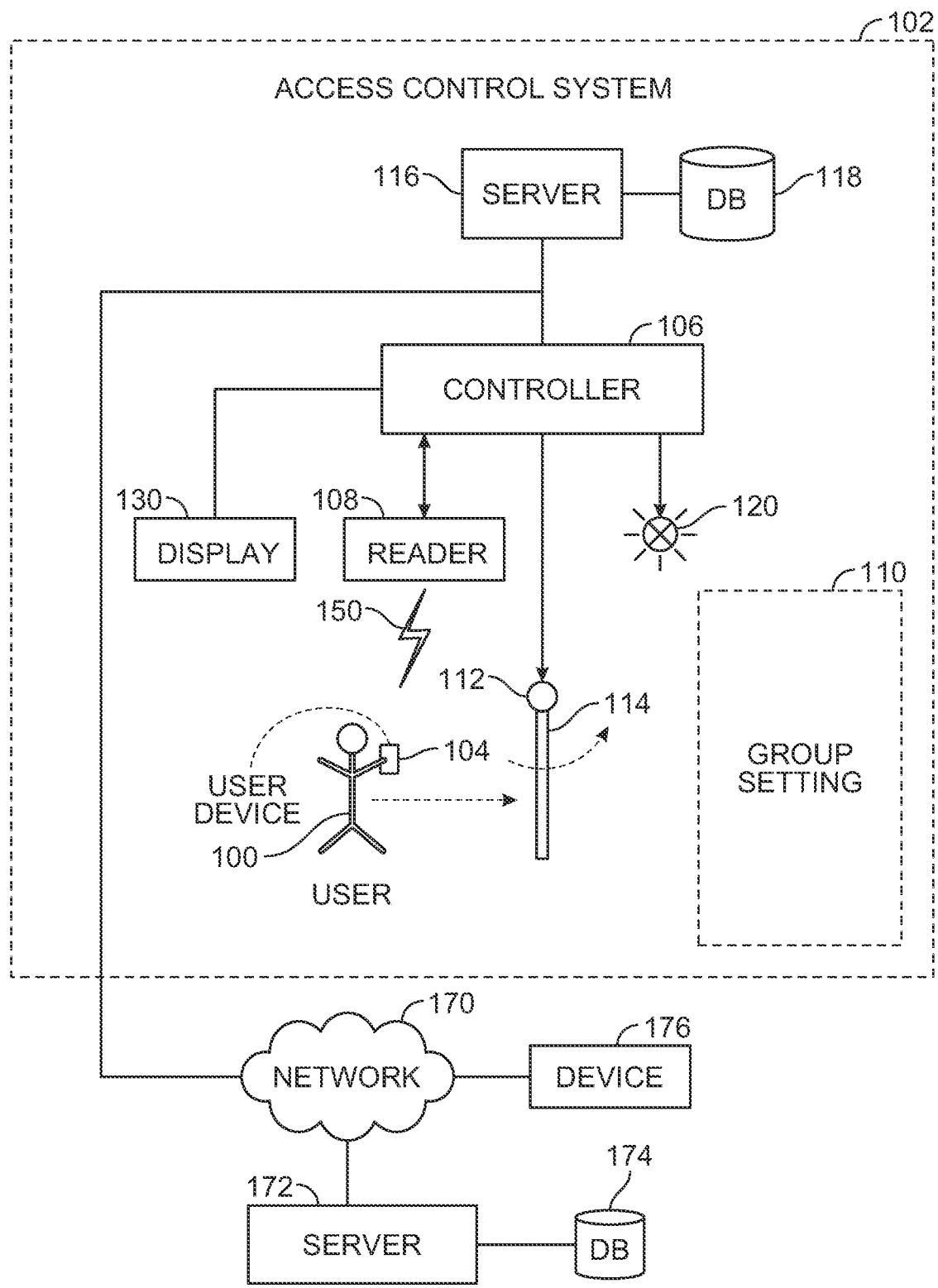
FIG. 1 is the schematic block diagram of the access control system for access control to a group setting for use in accurately tracking and informing of health and safety for group settings according to some embodiments.

As described in the Background section, under occupational safety and health laws, employers and other organizations may have duties to maintain safe operating environments. Those duties can include taking reasonable measures to prevent the spread of disease. For example, in order to prevent the outbreak of contagious diseases, organizations should take basic measures such as making tissues and antibacterial soap available. Encouraging hand washing, disinfecting, offering flu shots, and urging people to get immunizations are also good practices. Of course, other group settings may have the same or similar concerns and needs.

In late December 2019, several cases of pneumonia of unknown origin were reported from China, which in early January 2020 were announced to be caused by a novel coronavirus. This virus was later designated as severe acute respiratory syndrome coronavirus 2 (SARS-CoV-2) defined to be the causal agent of Coronavirus Disease 2019 (COVID-19). Despite attempts to contain the disease, the virus has spread globally and COVID-19 was declared a pandemic by the World Health Organization (WHO) in March 2020.

Various methods and systems for accurately tracking and informing of health and safety with respect to contagious illnesses for group settings are described herein. In some embodiments, a user score of a test for assessing a risk of a user of having or developing a contagious illness (e.g. COVID-19) may be obtained, for each user of a plurality of users entering in a group setting. A group score may be generated based on a plurality of user scores associated with the plurality of users in the group setting, including the user score of the user. The group score may indicate a group risk of a presence or development of the contagious illness in the group setting. The group score indicating the group risk of the presence or development of the contagious illness in the group setting may be communicated for display. In some embodiments, the user score may be obtained based on a reading of a user device of the user at an access control system for entry in the group setting.

In other embodiments, a score indicating a group risk of a presence or development of a contagious illness (e.g. COVID-19) in a group setting may be obtained, for each group setting of a plurality of group settings. The scores associated with the plurality of group settings may be communicated for display. Each score may be a group score which is obtained based on a plurality of user scores associated with a plurality of users in each group setting, and each user score may be obtained based on a reading of a user device of a user at an access control system used for entry into the group setting. The scores between group settings may be communicated for display (e.g. for comparative purposes). The plurality of group settings may be identified by their locations or names. At least a subset of the group settings may be grouped according to a group setting type, where locations or names of the group settings of the grouped subset of the same group setting type are communicated for display in association with the group scores.

In some embodiments, location-based techniques may be utilized in the accurate tracking and informing of health and safety for group settings for a mobile user device. In an example embodiment, a system may include a server configured to connect in a network and the mobile user device which is configured to connect in a mobile network for communications. The server may be configured to obtain a score indicating a group risk of a presence or development of a contagious illness (e.g. COVID-19) in a group setting and store the score in association with a location of the group setting, for each group setting of a plurality of group settings. The server may be further configured to obtain a current location of the mobile user device connected in the mobile network. The server may be further configured to communicate to the mobile user device a message alerting or otherwise indicating one of the plurality of group settings as a current high risk group setting that is associated with a score that is outside a limit set by a threshold value and with a location that is in proximity to the current location of the mobile user device.

As employers and other organizations may have duties to maintain safe operating environments, which can include taking reasonable measures to prevent the spread of disease, the techniques and mechanisms of the present disclosure can provide additional assurances of health and safety in group settings. In addition, the techniques and mechanisms of the present disclosure may leverage existing technology to minimize changes to existing devices, systems, and network architectures. Also, as group scores may be generated for display based on user scores from tests of users, and not include or maintain storage of the actual user scores from the tests of the users, compliance with Health Insurance Portability and Accountability Act (HIPAA) and/or other regulatory standards, policies, and practices is assured. Use of any sensitive test results or user scores of users in the network or system may be immediately discarded (e.g. deleted or cleared) after derivation of the group scores.

To better illustrate the example embodiments in relation to the figures, FIG. 1 is a schematic block diagram of an access control system 102 for access control to an area associated with a group setting 110, for use in accurately tracking and informing of health and safety for group setting 110. More particularly, access control system 102 may be configured for access control of a user 100 into the area associated with group setting 110 based on a reading of a user device 104 of user 100. Put another way, access control system 102 may operate to permit entry and exiting of user 100 into group setting 110 based on the reading of user device 104.

In some embodiments, the reading of user device 104 may also be used for obtaining a user score of a test for assessing a risk of user 100 having or developing a contagious illness. Further, a group score associated with group setting 110 may be generated based on a plurality of user scores associated with a plurality of users in group setting 110, which may include the user score of user 100. The group score associated with group setting 110 may indicate a group risk of a presence or development of the contagious illness in group setting 110. The group score associated with group setting 110 may be communicated for display.

As illustrated in FIG. 1, access control system 102 may include a controller 106, a reader 108, and an entry mechanism 114. Reader 108 may be configured to read data from user device 104. Data that are read from user device 104 of user 100 may be or include identity data of an identity of user 100, access control data for access control, or both. In some embodiments, as described later below, data read from user device 104 may include a user score of a test for assessing a risk of user 100 of having or developing a contagious illness. The type of reader 108 will depend on the system and the implementation of user device 104. Different types and varieties of devices are described herein and later in relation to FIGS. 11-12. In one example, reader 108 may be configured to read user device 104 which is an identification (ID) or access badge or other device according to its underlying technology. As another example, reader 108 may be configured to read user device 104 which is a mobile user device (e.g. a smartphone or a tablet computer) according to its underlying technology.

Entry mechanism 114 may be or include a mechanism for entry or access, which may include a door, a turnstile, a gate, an elevator, a parking gate, or other similar mechanisms. Controller 106 may be configured to communicate a signal to entry mechanism 114 for opening or closing of (or unlocking or maintaining locking of) entry mechanism 114 to permit or deny access of user 100 into group setting 110 based on access control data. In particular, controller 106 may communicate the signal to a switch 112 (e.g. a relay, a latch, electromechanical device, etc.) for opening or closing of (or unlocking or maintaining locking of) entry mechanism 114 to permit or deny access.

Access control system 102 may include a display 130 for displaying a group score associated with group setting 110. Access control system 102 may additionally or alternatively include an alert device 120 for permitting or denying access of user 100 into group setting 110 based on access control data. In one example, alert device 102 may be a lamp or light-emitting diode (LED). In another example, alert device 102 may be an audio device (e.g. a speaker). When permitting access of user 100 into group setting 110 based on the access control data, controller 106 may be configured to communicate a "permission" signal to alert device 120 (e.g. lighting the lamp "green" and/or audio signaling a positive sound). On the other hand, when denying access of user 100 into group setting 110 based on the access control data, controller 106 may be configured to communicate a "denial" signal to alert device 120 (e.g. lighting the lamp "red" and/or audio signaling a negative sound or buzz).

Group setting 110 may be managed by an organization for access control of users to and/or from group setting 110. The type of organization for access control of the users may depend on the type of group setting 110. Group setting 110 may be an indoor venue area associated with an indoor venue or an outdoor venue area association with an outdoor venue. Group setting 110 may be a building space area associated with a building space (a building or one or more rooms within the building). The building space area may be a commercial building space area, an employer building space area, a governmental building space area, or a residential building space area. For example, group setting 110 may be an area of an airport or an airplane, a shopping mall, a school, a courthouse or courtroom, a theatre, a concert stadium, a sports stadium, a park, or a festival, to name but a few. In addition, group setting 110 may be an area associated with a border crossing, for example, for entry into a (new) city, a county, a district, a state, a providence, or a country, etc.

In some embodiments, group setting 110 may correspond to a plurality of building spaces at different building space location areas that are managed by an organization (i.e. the same organization) having an organization name. In these cases, a group score associated with the group setting may be representative of a "health and safety reputation" of the organization that manages the various building spaces.

In some embodiments, controller 106 may interface with a server 116 having a database 118. In one example, server 116 may be a local server in a private local area network (LAN) or wireless LAN (WLAN) (e.g. based on IEEE 802.11 standards) of the organization that manages entry into group setting 110. In another, server 116 may be an external server that is external to the private LAN or WLAN of the organization that manages entry into group setting 110. The external server may be provided for access in a public network (e.g. the Internet) or a different private LAN, as examples. Database 118 could be co-located with server 116 or could be a remote database that is accessible to server 116 over a network. Database 118 may include any kind of storage device, including but not limited magnetic, optical, magneto-optical, and/or memory, including volatile memory and non-volatile memory.

In some embodiments, server 116 may interact with a server 172 having a database 174 and connected in a network 170. Network 170 and server 172 may be external to the network of server 116. A plurality of devices including a device 176 may be connected in network 170. In an example embodiment, device 176 may be a user device which is a desktop computer, a laptop computer, a smartphone, a tablet computer, etc. In another example embodiment, network 170 may be or include the Internet. In embodiments described herein, server 172 having database 174 may be used for the storage of multiple group scores from multiple systems associated with multiple group settings (e.g. access control system 102).

Figure 2:
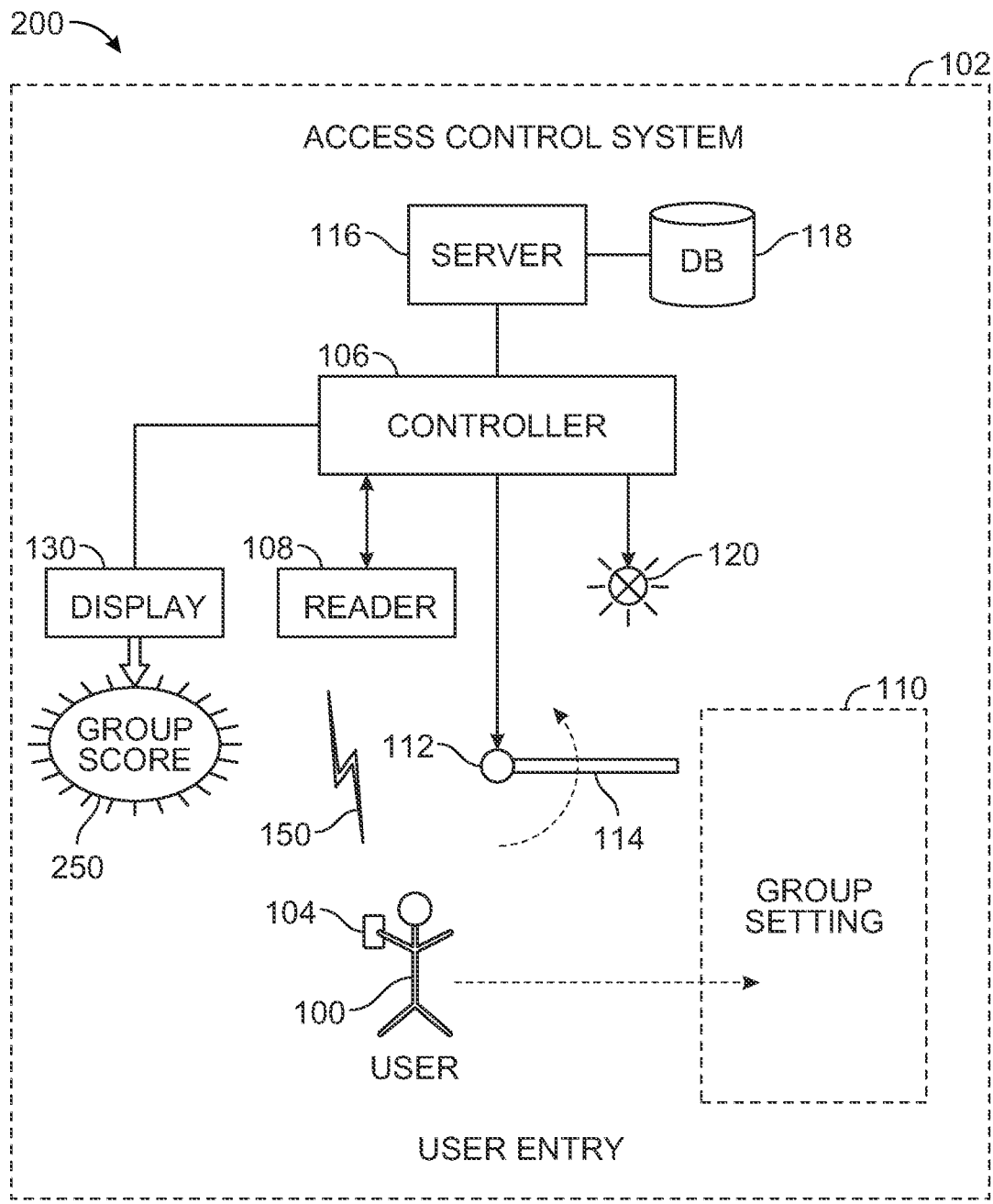
FIG. 2 is the schematic block diagram of the access control system of FIG. 1, illustrating a first example scenario where the access control system is operative to permit entry of the user into the group setting based on a reading of a user device of the user, for receiving a user score of a test for assessing a risk of the user of having or developing a contagious illness, and for generating a group score associated with the group setting for display, where the group score indicates a group risk of a presence or development of the contagious illness in the group setting.

FIG. 2 is the schematic block diagram of access control system 102 of FIG. 1, illustrating a first example scenario 200 where access control system 102 is operative to permit entry of user 100 into group setting 110 based on a reading of user device 104 of user 100. In the first example scenario, server 116 may obtain a user score of a test for assessing a risk of user 100 of having or developing a contagious illness based on the reading of user device 104. In addition, server 116 may generate a group score associated with group setting 110 based on a plurality of user scores associated with a plurality of users in group setting 110, including the user score of user 100. The group score may indicate a group risk of a presence or development of the contagious illness in group setting 110. Server 116 may cause the group score to be communicated for display in display 130. In the example embodiment shown in FIG. 2, server 116 causes a group score 250 to be communicated for display in display 130.

Figure 3:
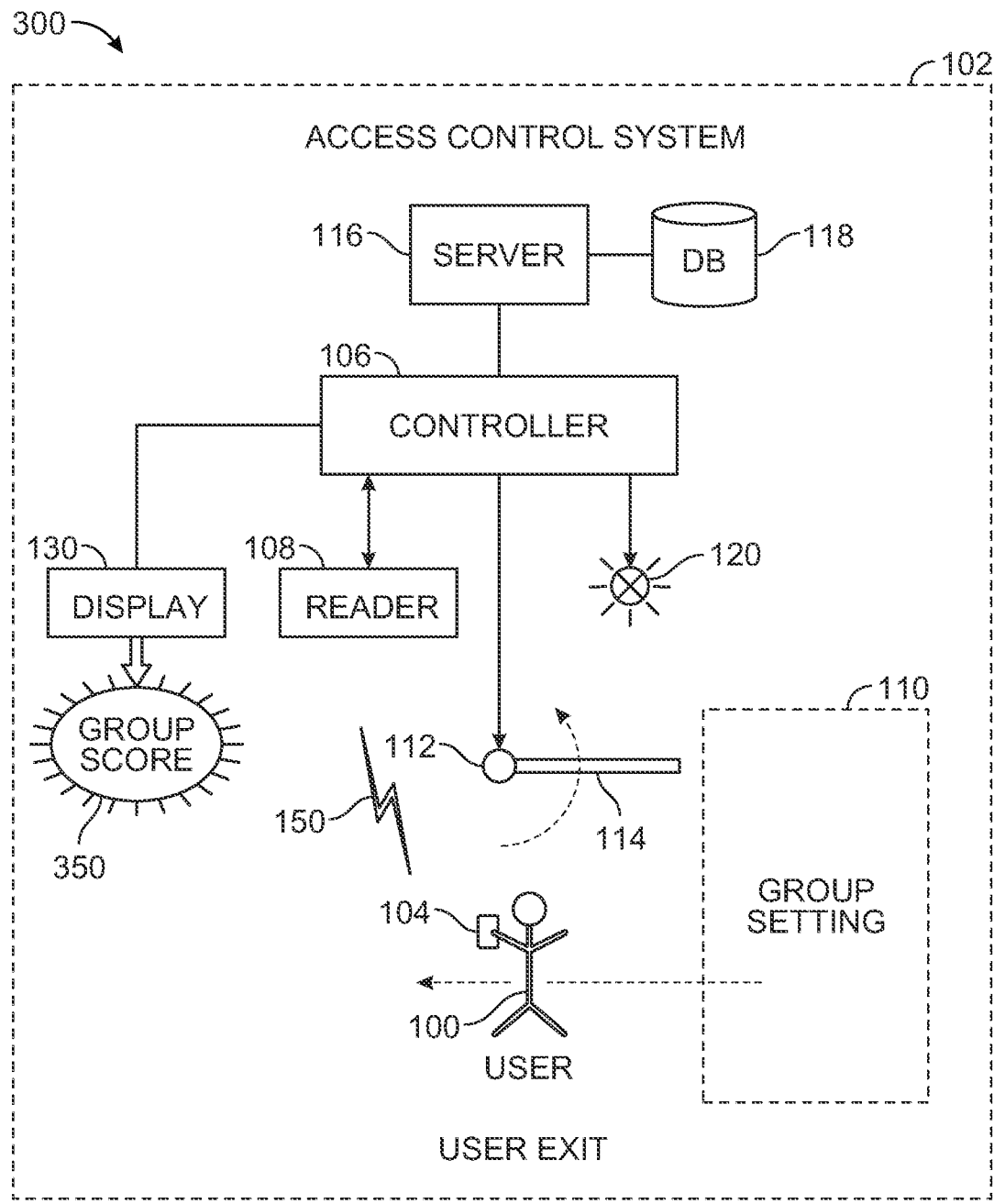
FIG. 3 is the schematic block diagram of the access control system of FIG. 1, illustrating a second example scenario where the access control system is operative to permit exit of the user from the group setting based on a reading of the user device of the user, for updating the group score associated with the group setting for display.

FIG. 3 is the schematic block diagram of access control system 102 of FIG. 1, illustrating a second example scenario 300 where access control system 102 is to permit the exiting of user 100 from group setting 110 based on a reading of user device 104 of user 100. In second example scenario 300, server 116 may identify user 100 as an existing user that is leaving group setting 110. In response, server 116 may update the group score associated with group setting 110 based on a plurality of remaining user scores (e.g. which exclude the user score of user 100) associated with a plurality of remaining users in group setting 110. The updated group score may indicate an updated group risk of a presence or development of the contagious illness in group setting 110. Server 116 may cause the updated group score to be communicated for display in display 130. In the example embodiment shown in FIG. 3, server 116 causes an updated group score 350 to be communicated for display in display 130.

In some embodiments, access control system 102 may obtain the user score of user 100 from user device 104 by the reading of user device 104. In other embodiments, one or more databases (e.g. database 118) may maintain storage of identifiers of users in association with user scores associated with the users. In this case, access control system 102 may receive from user device 104 the identifier of user 100 based on the reading of user device 104, and subsequently retrieve via server 116 the user score based on the identifier of user 100.

With this arrangement, as is apparent in relation to FIGS. 1-3, access control system 102 may operate to accurately track and inform of health and safety with respect to the contagious illness for group setting 110, for example, through group score 250.

Note that user scores and/or group scores may be associated with a variety of different ranges of values and/or formats, and may be derived or generated based on a variety of different types of resulting data, test results, or scores, as will be described herein. The user scores and/or group scores may be fashioned according to the specific underlying techniques utilized and may be functionally dependent on them. In some cases, lower scores may indicate higher risks and higher scores may indicate lower risks; in other cases, however, lower scores may indicate lower risks and higher scores may indicate higher risks. In other cases, user scores and/or group scores may be in the form of more generalized, discretized values or indicators, such as HIGH RISK, MEDIUM RISK, or LOW RISK values or indicators.

Figure 4:
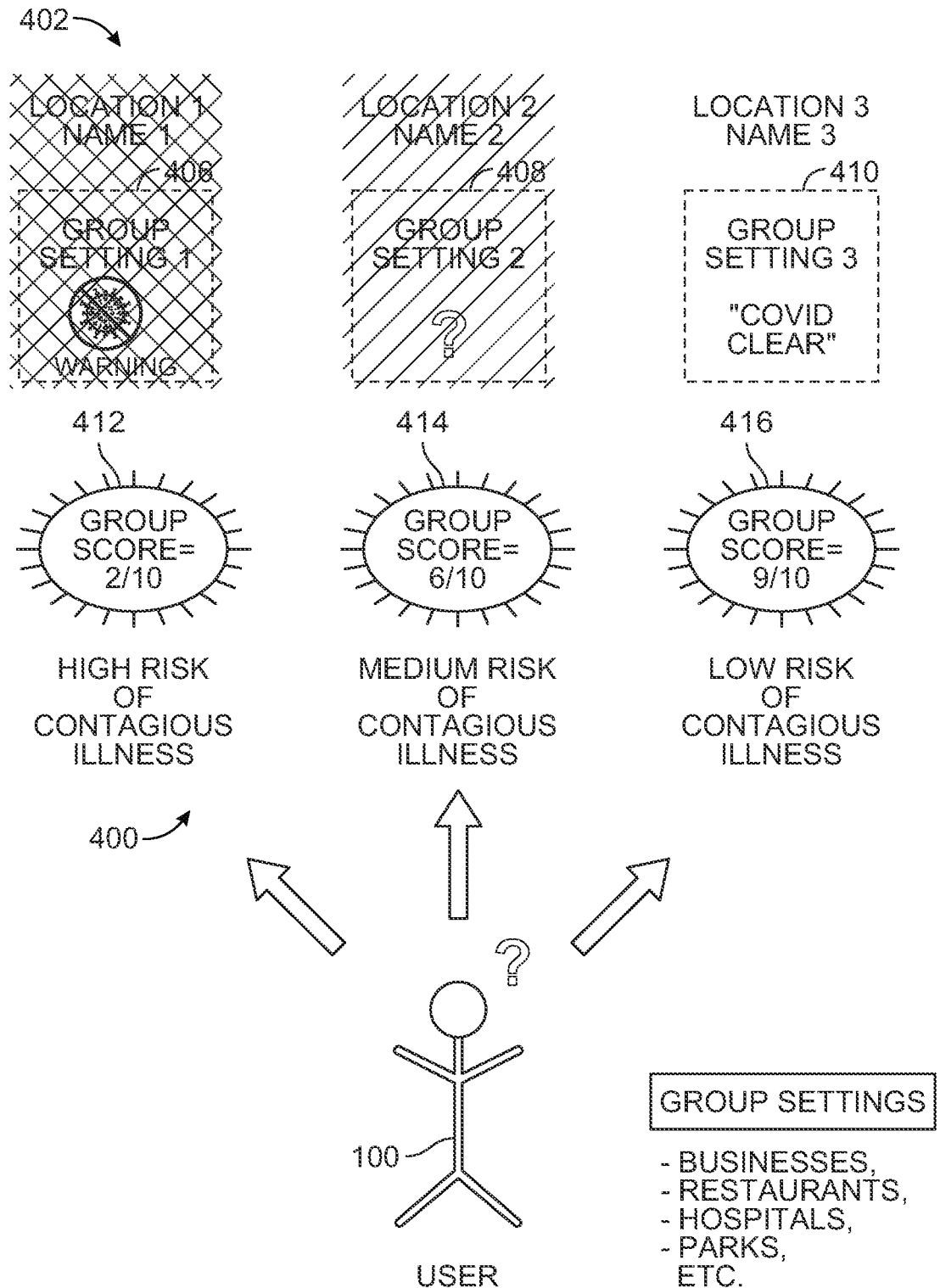
FIG. 4 is an illustrative scenario depicting the displaying of a plurality of group scores associated with a plurality of group settings for informing the user of the group risks of the presence or development of the contagious illness in the group settings in a comparative manner.

FIG. 4 is an illustrative scenario 402 depicting a display of a plurality of group scores 400 associated with a plurality of group settings 402 for informing user 100 of the group risks related to the presence or development of the contagious illness in the group settings 402. In illustrative scenario 402, the plurality of group settings 402 include a group setting 406 associated with a location 1/name 1, a group setting 408 associated with a location 2/name 2, and a group setting 410 associated with a location 3/name 3.

User 100 may be informed of the plurality of group scores 400 (e.g. group scores 412, 414, and 416) associated with the plurality of group settings 402 by their display. Group score 412 associated with group setting 406 is indicated to be 2 out of 10 (2/10), which is a low score which may indicate a high risk of the presence or development of the contagious illness in group setting 406. Group score 414 associated with group setting 408 is indicated to be 6 out of 10 (6/10), which is a medium score which may indicate an unknown or questionable risk of the presence or development of the contagious illness in group setting 408. Group score 416 associated with group setting 410 is indicated to be 9 out of 10 (9/10), which is a high score which may indicate a low risk of the presence or development of the contagious illness in group setting 410.

In one example, group settings 406, 408, and 410 of FIG. 4 may all be of the same group setting type (e.g. all restaurants, or all theatres, or all schools). Given the above, and all else being equal, user 100 may choose group setting 410 for entry instead of group settings 406 and 408.

Figure 5:
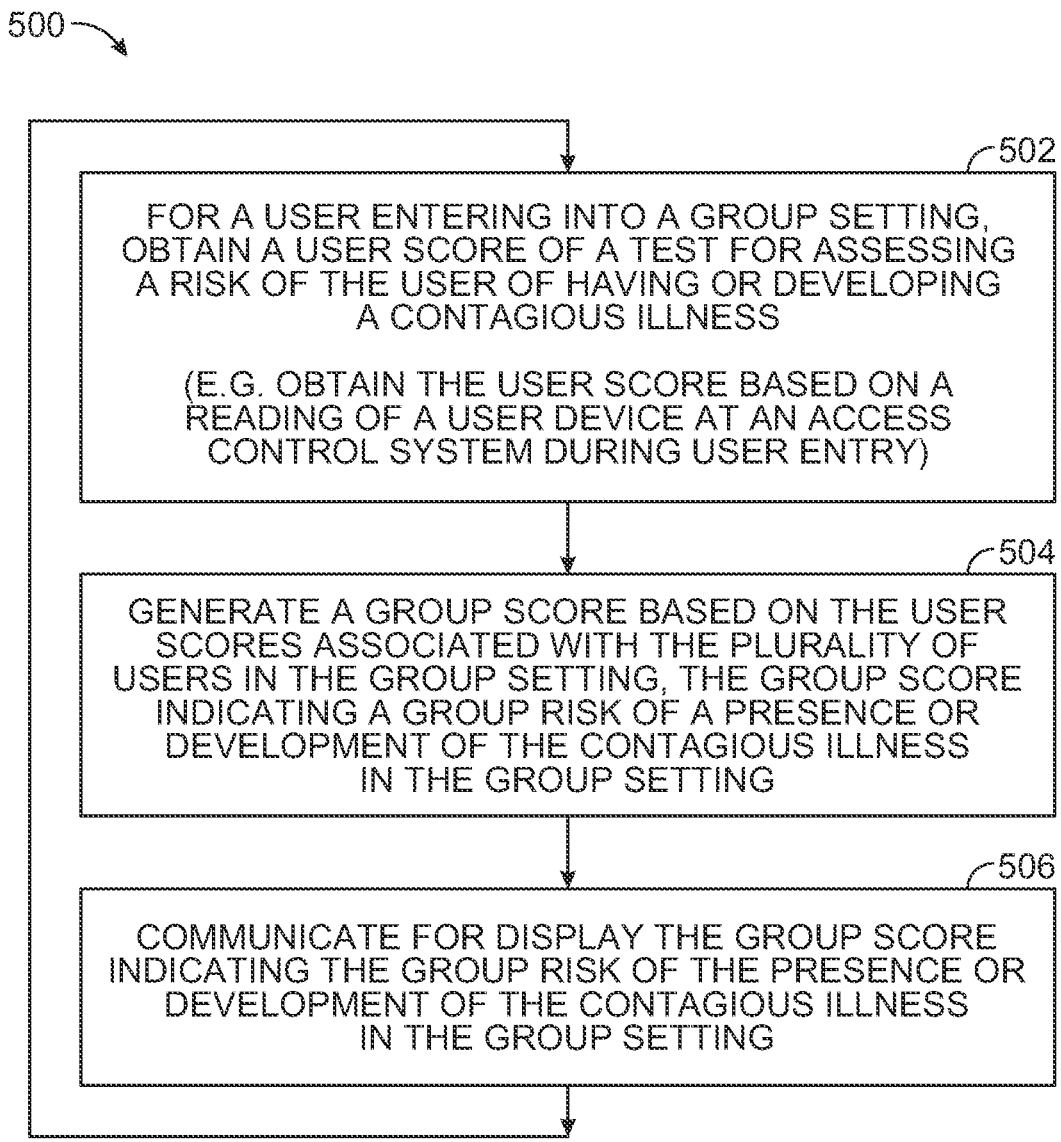
FIG. 5 is a flowchart for describing a method for use in accurately tracking and informing of health and safety for a group setting according to some embodiments, which may be performed by or with use of the access control system shown and described in relation to FIGS. 1-3.

FIG. 5 is a flowchart for describing a method 500 for use in accurately tracking and informing of health and safety for a group setting according to some embodiments. Method 500 shown in FIG. 5 may be performed by the access control system shown and described in relation to FIGS. 1-3 (e.g. server 116). Method 500 may be embodied in a computer program product having a non-transitory computer readable medium and instructions stored in the non-transitory computer readable medium, where the instructions are executable by the server to perform steps of method 500.

In the embodiment of FIG. 5, method 500 begins with a step 502. At step 502, for a user entering into a group setting, the server may obtain a user score of a test for assessing a risk of the user of having or developing a contagious illness. In some embodiments, the server may obtain the user score based on a reading of a user device of the user at an access control system for user entry into the group setting. Next, method 500 may proceed to a step 504, where the server may generate a group score based on user scores associated with a plurality of users in the group setting, including the user score of the user. The group score may indicate a group risk of a presence or development of the contagious illness in the group setting. Next, method 500 may proceed to a step 506, where the server may communicate for display the group score indicating the group risk of the presence or development of the contagious illness in the group setting. Next, method 500 may proceed to repeat for each entering user of a plurality of entering users entering in the group setting, where the server updates the group score and communicates for display the updated group score accordingly.

In an example embodiment of step 506 of method 500, the group score may be communicated for display in a display of the group setting (see e.g. display 130 of FIG. 1). In another example embodiment of step 506, the group score may be communicated for display by sending a message including the group score to a device having a display (see e.g. device 176 of FIG. 1). In yet another example embodiment of step 506, the group score may be communicated for display by posting or publishing the group score in association with a location or name of the group setting on a website (see e.g. server 172 of FIG. 1).

In some embodiments of method 500, the obtaining, the generating, and the communicating may be regularly repeated, for communicating for display a real-time group score indicating a real-time group risk of the presence or development of the contagious illness in the group setting.

Figure 6:
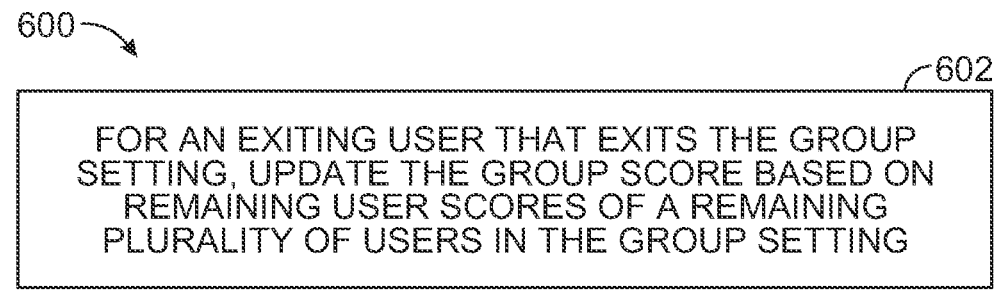
FIG. 6 is a flowchart for describing a method for use in accurately tracking and informing of health and safety for a group setting according to some embodiments, which may be performed by or with use of the access control system of FIGS. 1-3 and together with the method shown and described in relation to FIG. 5.

FIG. 6 is a flowchart for describing a method 600 for use in accurately tracking and informing of health and safety for a group setting according to some embodiments. Method 600 shown in FIG. 6 may be performed by or with use of the access control system of FIGS. 1-3 (e.g. server 116) and together with the method 500 shown and described in relation to FIG. 5. In the embodiment of FIG. 6, method 600 begins with a step 602. At step 602, for an exiting user that leaves the group setting, the server may update the group score based on remaining user scores of a remaining plurality of users in the group setting. Method 600 may proceed to repeat for each exiting user of a plurality of exiting users that leaves the group setting, where the server may communicate for display the updated group score accordingly.

FIG. 7 is an illustrative example of a display item 700 associated with a group score indicating a group risk of a presence or development of a contagious illness in a group setting. In the illustrative example of FIG. 7, display item 700 includes a name and a location of the group setting, which is "KARIN'S KAFE" located at "ADDRESS 1/GEO-LOCATION 1." Display item 700 may also indicate a group setting type associated with the group setting, which is a "COFFEE SHOP." Display item 700 includes a group score of "9/10" which may be indicative of a low risk of the presence or development of the contagious illness at the COFFEE SHOP named KARIN's KAFE which is located at ADDRESS 1/GEOLOCATION 1.

FIG. 8 is an illustrative example of a display item 800 associated with a group score indicating a group risk of a presence or development of a contagious illness in a group setting. In the illustrative example of FIG. 8, display item 800 includes a name and a location of the group setting, which is "JOHN INC" located at "ADDRESS 2/GEOLO-CATION 2." Display item 800 may also indicate a group setting type associated with the group setting, which is a "COMPANY/BUSINESS." Display item 800 includes a group score of "3/10" which may be indicative of a high risk of the presence or development of the contagious illness at the COMPANY/BUSINESS named JOHN INC which is located at ADDRESS 2/GEOLOCATION 2.

FIG. 9 is a flowchart for describing a method 900 for use in accurately tracking and informing of health and safety for a group setting according to some embodiments. Method 900 shown in FIG. 9 may be performed by or with use of the access control system of FIGS. 1-3 (e.g. server 116) and together with the methods described in relation to FIGS. 5 and 6. In particular, method 900 of FIG. 9 may be used for performing step 504 of method 500 of FIG. 5.

In the embodiment of FIG. 9, method 900 begins with a step 902. Prior to this step, the server may obtain, over a period of time, a plurality of sample group scores associated with the group setting over the period of time. In one embodiment, the plurality of sample group scores may be user-by-user generated group scores (i.e. group scores that are updated in response to each user entry into or exit from the group setting). At step 902, the server may generate an average group score based on the plurality of sample group scores associated with the group setting obtained over the period of time. The average group score may indicate an average group risk of the presence or development of the contagious illness in the group setting. As some examples, the average group scores may be generated as a mean, a mode, a median, or a moving average of the plurality of sample group scores. As other examples, the period of time may correspond to a period of an hour, a day, a week, a month, or a year. Accordingly, the group score associated with the group setting which is communicated for display may indicate an average over the period of time (e.g. in contrast to a real-time, user-by-user generated group score).

FIG. 10 is a flowchart for describing a method 1000 for use in accurately tracking and informing of health and safety for a group setting according to some embodiments. Method 1000 shown in FIG. 10 may be performed by or with use of the access control system of FIGS. 1-3 (e.g. server 116) and together with the methods described in relation to FIGS. 5 and 6. In particular, method 1000 of FIG. 10 may be used for performing step 504 of method 500 of FIG. 5.

In the embodiment of FIG. 10, method 1000 begins with a step 1002. Prior to this step, the server may obtain, over a period of time, a plurality of sample group scores associated with the group setting over the period of time. In one embodiment, the plurality of sample group scores may be user-by-user generated group scores (i.e. group scores that are updated in response to each user entry into or exit from the group setting). At step 1002, the server may identify or detect a peak value of the group score associated with the group setting over the period of time. The peak value of the group score may indicate a peak group risk of the presence or development of the contagious illness in the group setting over the period of time. As some examples, the period of time may correspond to a period of an hour, a day, a week, a month, or a year. Accordingly, the group score associated with the group setting which is communicated for display may indicate a detected peak (i.e. indicating peak high risk) over the period of time (e.g. in contrast to a real-time, user-by-user generated group score).

Figure 11:
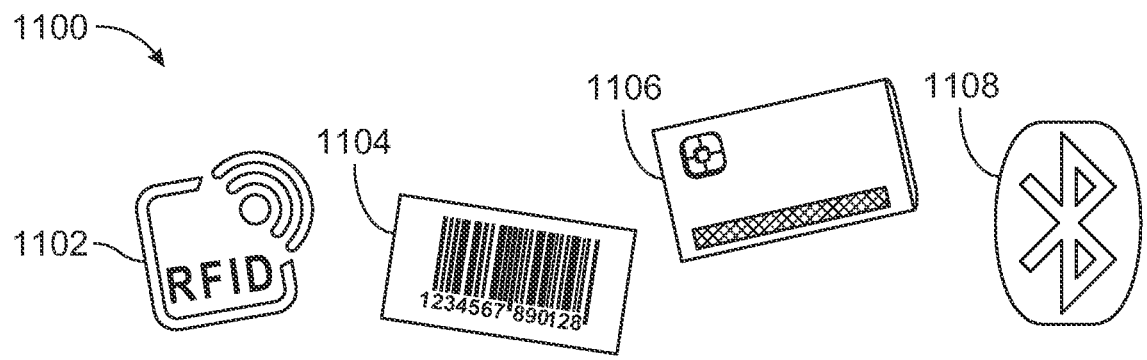
FIG. 11 is an illustration of a variety of different types of devices which may be utilized as or by the user device of the user.

As described earlier above, the user device may be an ID or access badge or device associated with the user. With reference now to FIG. 11, an illustrative representation of a variety of different types of devices 1100 which may be utilized as, with, or in a user device for access control are shown, in accordance with various embodiments. In FIG. 11, devices 1100 may include a Radio Frequency Identification (RFID) tag or device 1102, an access card 1104 having a bar code, a magnetic swipe card 1106 which may also be a smart card, and a Bluetooth device 1108 (e.g. based on IEEE 802.15) which may be included in a mobile user device or a stand-alone peripheral device, to illustrate but a few.

Thus, a variety of different types of devices may be utilized as, with, or in the user device associated with the user in various embodiments. Accordingly, magnetic or "swipe" cards for swipe card access systems may be utilized, proximity cards for proximity card access systems may be utilized (e.g. using 125 KHz proximity technology), smart cards for system card access systems may be utilized (e.g. using 13.56 KHz proximity technology), QR codes for QR code-based access systems, and so on. Swipe card access systems may utilize magnetic cards for basic, low security access control. Proximity cards may include printable PVC cards, clamshell cards, and others. Smart card access systems may provide more security and utilize contactless smart card technology to provide identification, authentication, and storage of information on the card (e.g. where the card includes a microchip and memory).

Figure 12:
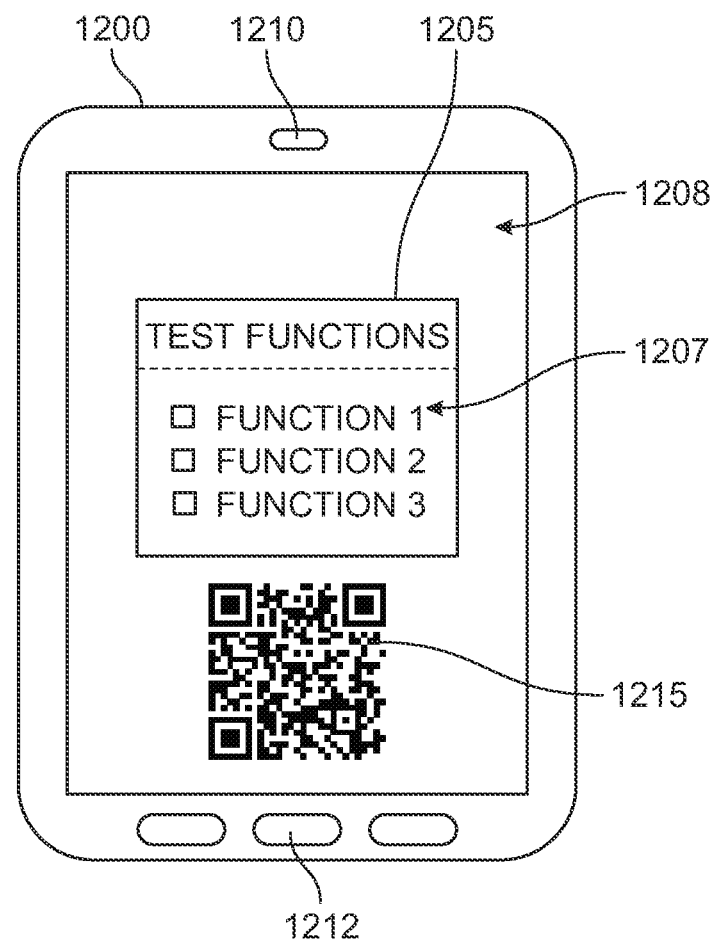
FIG. 12 is an illustration of a user device which is one type of a mobile user device which may have one or more test functions or illness risk factor assessment functions according to some embodiments.

FIG. 12 is an illustration of one type of a user device which, in this embodiment, is a mobile user device 1200. In particular, mobile user device 1200 of FIG. 12 is shown to be a smartphone or a tablet computer (e.g. a handheld device). In FIG. 12, mobile user device 1200 includes a user interface which may include a touch screen display 1208, a speaker 1210 and a microphone 1212. In some embodiments, mobile user device 1200 may include an application 1205 having test functions 1207 for a test for assessing a risk of the user of having or developing a contagious illness. The test functions 1207 may be illness risk factor assessment functions, which may alternatively be referred to as symptom detection functions.

In some embodiments, as illustrated in FIG. 12, mobile user device 1200 may cause QR code data 1215 for providing a user score of the user to be displayed in the touch screen display. QR code data 1215 for providing the user score may be derived based on a test result or score of a test for the user, and may be displayed for being read by a reader of an access control system (see e.g. FIGS. 1-3). Thus, the display or touch screen display of mobile user device 1200 for displaying QR code data may be used for providing the user score of the user.

Figure 13:
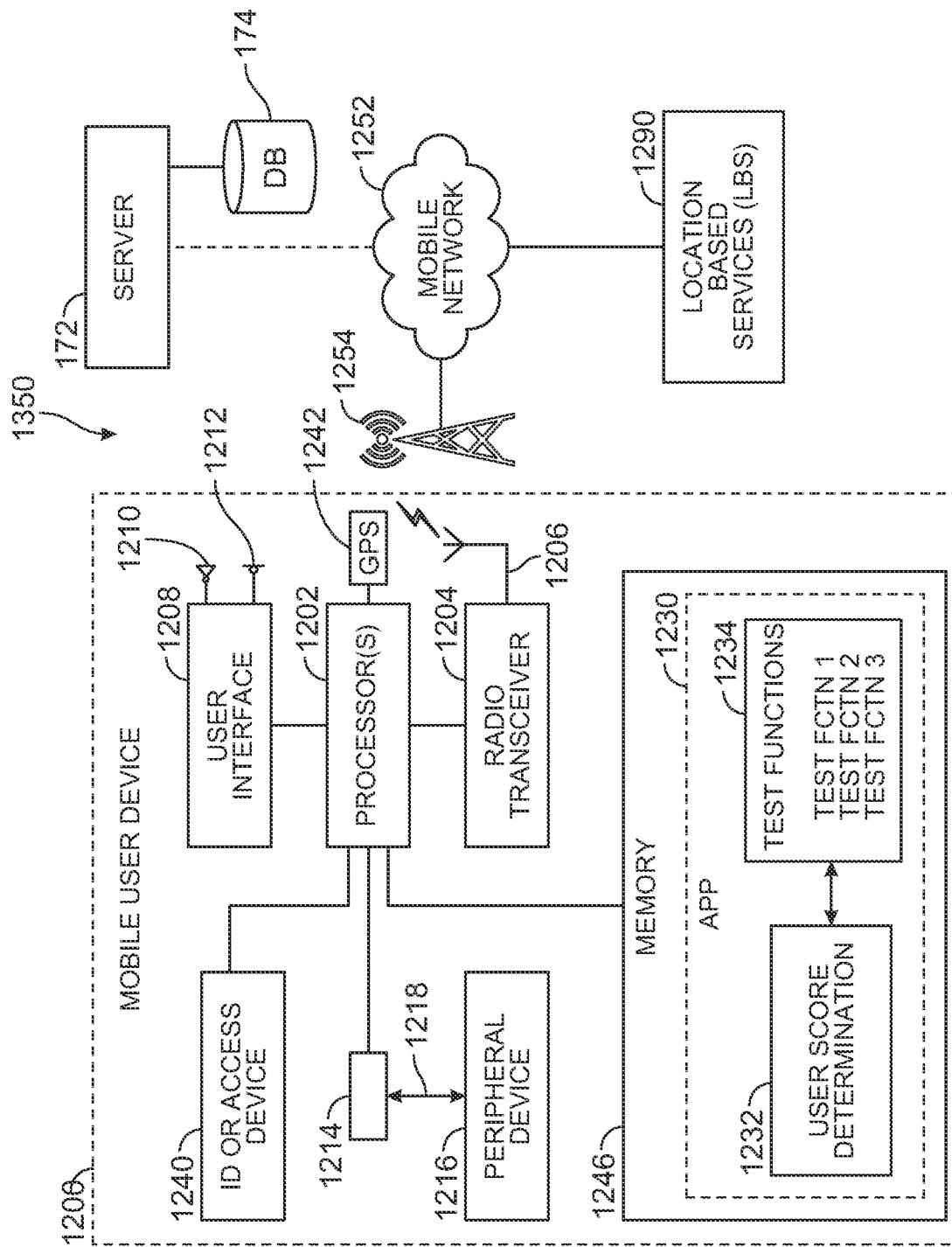
FIG. 13 is a schematic block diagram of a mobile user device which may connect in a mobile network for communications according to some embodiments.

FIG. 13 is a schematic block diagram of mobile user device 1200 which may connect in a mobile network 1252 for communications in a communication system 1350 according to some embodiments. Mobile user device 1200 may include one or more processors 1202, a memory 1246, and a radio transceiver 1204 with an antenna 1206. Mobile user device 1200 may also include user interface 1208, speaker 1210, and microphone 1212 as previously identified in relation to FIG. 12. Radio transceiver 1204 is configured to connect with mobile network 1252 via a base station 1254 to provide mobile user device 1200 with mobile communications. In some embodiments, mobile user device 1200 may include a peripheral interface for connecting a peripheral device 1216 to mobile user device 1200 via a connection or connector 1218. With use of a global positioning system (GPS) device 1242 of mobile user device 1200, one or more servers 1290 for location-based services (LBS) servers 1290 in mobile network 1252 may operate to provide location services for mobile user device 1200.

Memory 1246 may include an application 1230 having a user score determination function 1232 for maintaining health and safety standards according to the present disclosure. One or more processors 1202 may operate to execute applications of mobile user device 1200, including application 1230 having user score determination function 1232. User score determination function 1232 may interact with application 1205 having the test functions for the test for assessing the risk of the user of having or developing the contagious illness. The test functions of application 1205 may be illness risk factor assessment functions, which may alternatively be referred to as symptom detection functions.

Figure 14:
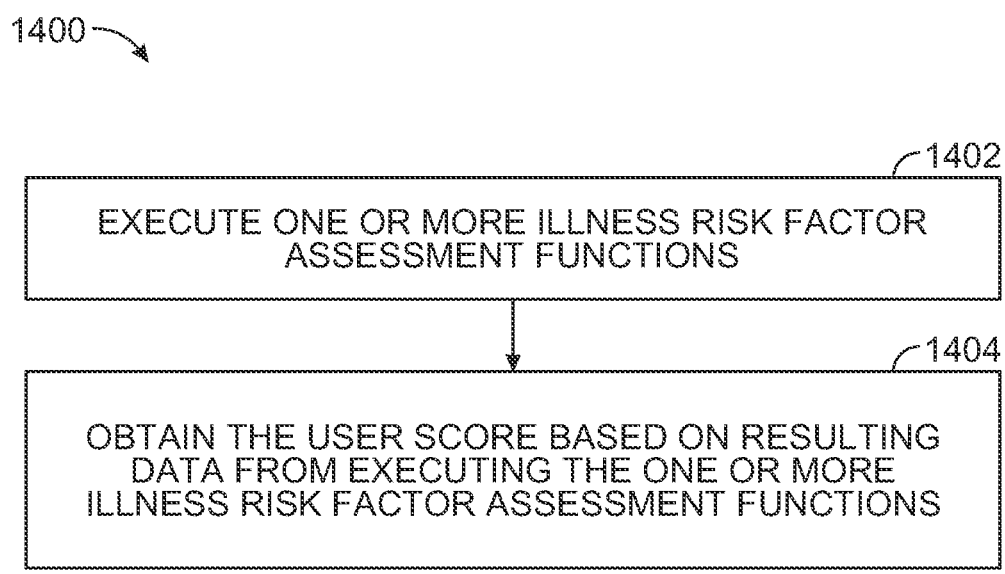
FIG. 14 is a flowchart for describing a method for obtaining a test result or score based on resulting data from executing the one or more illness risk factor assessment functions of the mobile user device according to some embodiments.

FIG. 14 is a flowchart for describing a method 1400 for obtaining a test result or score based on resulting data from executing one or more illness risk factor assessment functions according to some embodiments. In some embodiments, method 1400 shown in FIG. 14 may be performed by a mobile user device (e.g. the mobile user device 1200 of FIGS. 12-13). In some cases, in particular, method 1400 shown in FIG. 14 may be performed by one or more processors of the mobile user device. In these embodiments, the mobile user device may have an application which includes one or more illness risk factor assessment functions which form all or part of a test for assessing a risk of the user of having or developing a contagious illness. As described earlier, the illness risk factor assessment functions may alternatively be referred to as symptom detection functions.

In this embodiment, method 1400 begins with a step 1402. At step 1402, the one or more illness risk factor assessment functions of the mobile user device may be executed. In one example, each one of the one or more illness risk factor assessment functions of the mobile user device may be executed in a serial manner with assistance of the user. Next, method 1400 may proceed to a step 1404, where the test result or score of the test may be obtained based on resulting data from executing the one or more illness risk factor assessment functions.

In some embodiments of method 1400, at step 1404, the test result or score of the test may be obtained based on combining the resulting data from each one of the one or more illness risk factor assessment functions. For example, the resulting data from each one of the one or more illness risk factor assessment functions may be combined or averaged. The access control data may then be derived, determined or retrieved based on the test result or score of the test.

At least some of the one or more illness risk factor assessment functions may be utilized to identify or detect a symptom of the user at the mobile user device 900. A user having a contagious illness may have a range of different symptoms, ranging from mild to severe. For example, individuals with COVID-19 are associated with a wide range of different symptoms, from mild to severe, which surface after a period of time after exposure to the virus (e.g. 2-14 days). Symptoms associated with COVID-19 may include a cough, a shortness of breath or difficulty breathing, a fever, chills, a sore throat, a new loss of taste or smell, muscle pain, as well as other symptoms.

In some embodiments of method 1400 of FIG. 14, the one or more illness risk factor assessment functions provided at the mobile user device may include a temperature detection function which is based on a temperature of the user; an image-based symptom recognition function which is based on facial characteristics of the user, using a camera of the mobile user device; an audio-based symptom recognition function which is based on qualities of voice, nasal, or congestion of the user, using an audio recorder of the mobile user device; or a pulse oximeter function which is based on a blood oxygenation of the user.

Figure 15:
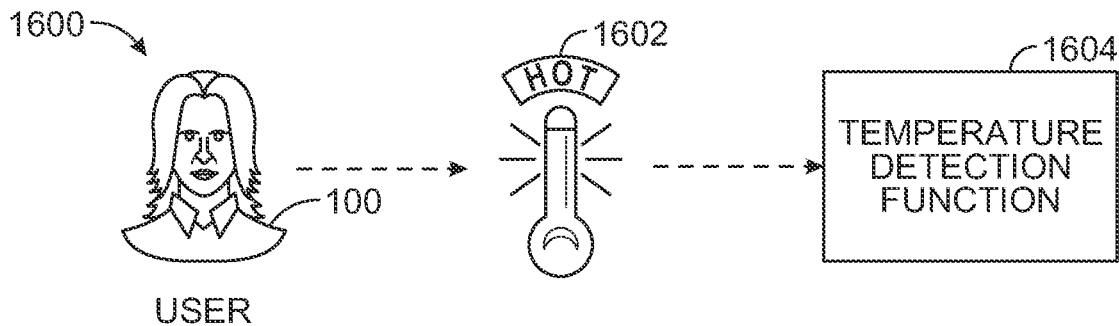
FIG. 15 is an illustrative scenario of the use of a temperature detection function which may be executed by the mobile user device.
Figure 16:
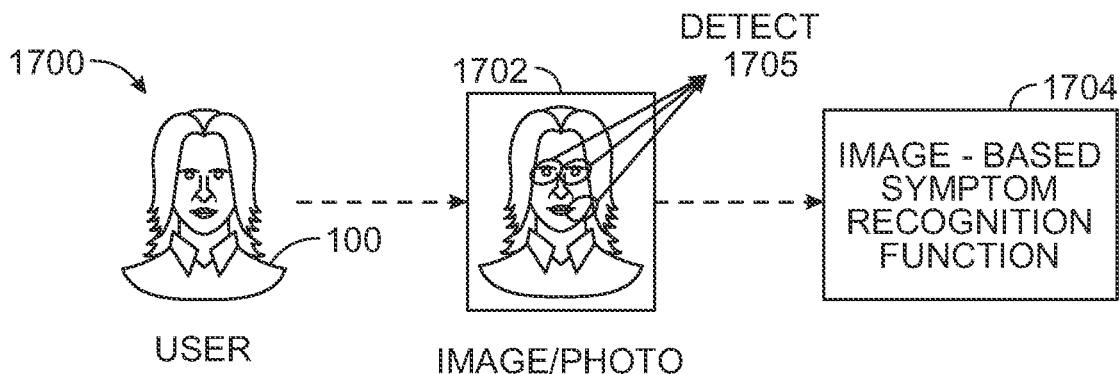
FIG. 16 is an illustrative scenario of the use of an image-based symptom recognition function which may be executed by the mobile user device.
Figure 17:
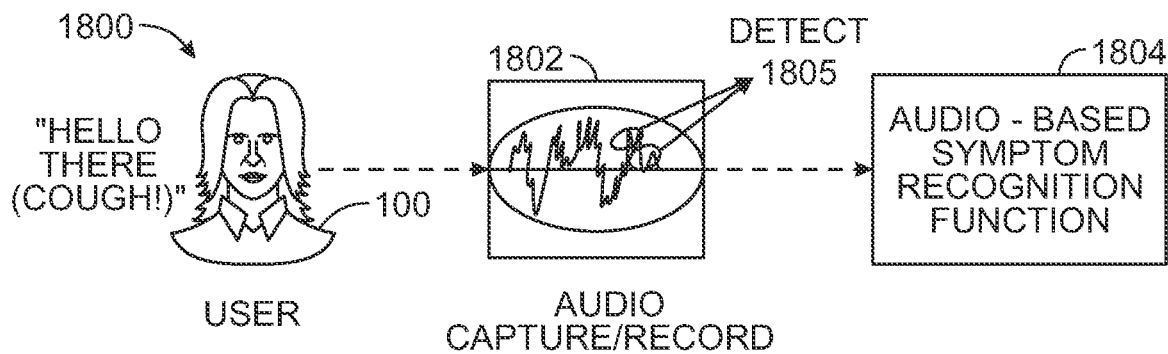
FIG. 17 is an illustrative scenario of the use of an audio-based symptom recognition function which may be executed by the mobile user device.

To better illustrate the techniques and mechanisms of the example embodiments, FIGS. 15-17 are illustrative scenarios of the use of various illness risk factor assessment functions of the mobile user device.

Beginning with FIG. 15, an illustrative scenario 1500 of the use of a temperature detection function 1504 of the mobile user device is shown. Temperature detection function 1504 operates to obtain a temperature reading 1502 of user 100 and determine, based on temperature reading 1502, a score corresponding to an illness risk factor for assessing the risk of user 100 of having or developing the contagious illness. In some embodiments, temperature detection function 1504 may be executed with use of an electronic thermometer or other sensor for reading the temperature of user 100. In some embodiments, an electronic thermometer or other sensor may be connected to the mobile user device as a peripheral device (see e.g. peripheral device 916 having connection 918 with mobile user device 900). In other embodiments, a fingerprint thermometer may be provided with use of a fingerprint scanner of the mobile user device; the fingerprint scanner may be the existing, built-in fingerprint scanner of the mobile user device.

In FIG. 16, an illustrative scenario 1600 of the use of an image-based symptom recognition function 1604 of the mobile user device is shown. Image-based symptom recognition function 1604 may be for detecting symptoms of the contagious illness based on facial characteristics of the user. Image-based symptom recognition function 1604 of the mobile user device may be executed with use of a camera of the mobile user device. In one example, the camera is the existing, built-in camera of the mobile user device. Here, image-based symptom recognition function 1604 may cause an image or photo 1602 of the face of user 100 to be captured, and identify or detect one or more symptomatic features 1602 associated with the contagious illness based on the image or photo 1602. Image-based symptom recognition function 1604 may then determine, based on the one or more symptomatic features 1602, a score corresponding to an illness risk factor for assessing the risk of the user of having or developing the contagious illness.

In FIG. 17, an illustrative scenario 1700 of the use of an audio-based symptom recognition function 1704 of the mobile user device is shown. Audio-based symptom recognition function 1704 may be for detecting symptoms of the contagious illness based on audio qualities, i.e. qualities of voice, nasal, or congestion of user 100. Audio-based symptom recognition function 1704 of the mobile user device may be executed with use of an audio recorder of the mobile user device. In one example, the audio recorder may be the existing, built-in audio recorder of the mobile user device. Here, audio-based symptom recognition function 1704 may cause an audio clip 1702 of user 100 to be captured (e.g. where user 100 is speaking into the mobile user device), and then identify or detect one or more symptomatic features 1705 associated with the contagious illness based on audio clip 1702. Audio-based symptom recognition function 1704 may then determine, based on the one or more symptomatic features 1702, a score corresponding to an illness risk factor for assessing the risk of the user of having or developing the contagious illness.

In an example embodiment, the pulse oximeter function of the mobile user device may be configured to measure the proportion of oxygenated hemoglobin in the blood in pulsating vessels, especially the capillaries of the finger or ear. In particular, the pulse oximeter function may determine a heart rate and a peripheral capillary oxygen saturation (SpO2) of the user. The pulse oximeter function may determine, based on the heart rate and/or SpO2, a score corresponding to an illness risk factor for assessing the risk of the user of having or developing the contagious illness. For measurements, the pulse oximeter function may prompt the user to place his or her finer over the camera and lens while measurements are taken.

Notably, in some embodiments, the test result or score may be based on an actual "lab" test for the contagious illness (e.g. COVID-19). Currently, there are two kinds of tests available for COVID-19: a viral test and an antibody test. A viral test may indicate if you currently have an infection with SARS-CoV-2, the virus that causes COVID-19. Molecular and antigen tests are types of viral tests, which may also be referred to as diagnostic tests. An antibody test may indicate if an individual has previously had an infection with SARS-CoV-2. This type of test may also be referred to as a serological test. In one example, a test kit may be provided for detecting a presence or absence of ribonucleic acid (RNA) material from a virus (e.g. SARS-CoV-2). The test kit may be in the form of an at-home test kit. Different types of authorized at-home test kits are commercially available from several different reputable companies.

If the test result of a viral test is positive for COVID-19, the individual should be informed of protective measures to take, especially if the individual is noticeably sick or has symptoms, or caring for someone else. If the test result of the viral test is negative for COVID-19, the individual was (likely) not infected at the time the sample was collected. However, that does not necessary mean that the individual will not get sick. The test result only means that the individual did not have COVID-19 at the time of testing. The individual might test negative if the sample was collected early in the infection but then test positive later on.

On the other hand, an antibody test may indicate if an individual has previously had SARS-CoV-2. The antibody test may be processed in a health care laboratory. In one example, the antibody test may test for an antibody referred to as immunoglobulin G (IgG) to indicate if an individual has previously had SARS-CoV-2. In this example, test results of the antibody test may correspond to one of four different findings: Pending, Not Detected, Borderline, or Detected. In a finding of "Pending," the health care laboratory may still be processing a blood sample of an individual. In a finding of "Not Detected" (or "negative"), IgG antibodies to SARS-CoV-2 were not detected in the blood of the individual. Note that a negative result for IgG antibodies does not rule out a SARS-CoV-2 infection, particularly for individuals who have been in contact with the virus (e.g. the individual's immune function may have been suppressed by other health issues or the antibody level is too low for the test to detect). In a finding of "Borderline," IgG antibodies to SARS-CoV-2 were detected, but at a level that was too low to determine whether the individual has had a past infection. Note that a borderline result may indicate a very early infection or a prior infection with one or more other coronaviruses. In a finding of "Detected," IgG antibodies to SARS-CoV-2 were detected in the blood of the individual at a level that was sufficient to determine that the individual has had a past infection with SARS-CoV-2.

Figure 18:
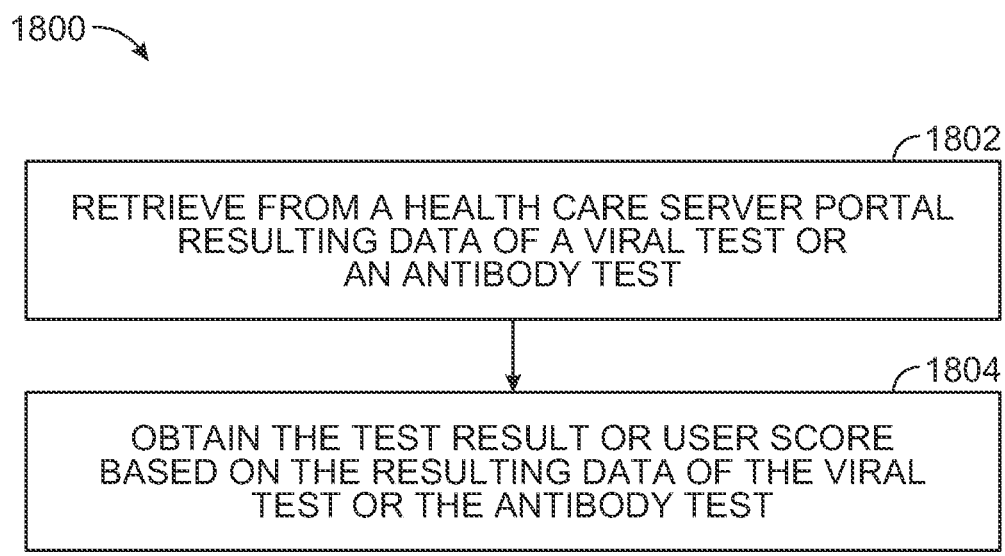
FIG. 18 is a flowchart for describing a method for obtaining a test result or score based on resulting data of a viral test or an antibody test obtained from a health care server portal by the mobile user device according to some embodiments.

FIG. 18 is a flowchart for describing a method 1800 for obtaining a test result or score based on resulting data of a viral test or an antibody test according to some embodiments. A viral test or an antibody test for a user may be processed at a health care laboratory based on a sample of the user (e.g. a swab from the nose or the throat of the user, a blood sample of the user, etc.). Resulting data of the viral test or the antibody test may be generated based on the sample. The resulting data may be provided in the form of electronic data which is made privately available for viewing or retrieval via a health care server portal.

In this embodiment, method 1800 begins with a step 1802. At step 1802, the mobile user device may retrieve, from the health care server portal, the resulting data of the viral test or the antibody test of the user. Next, method 1800 may proceed to a step 1804, where the test result or score of the test may be obtained based on the resulting data of the viral test or the antibody test.

In one example of method 1800, at step 1804, the resulting data of the viral test or the antibody test is the test result or score. In another example of method 1800, at step 1804, the test result or score of the test may be obtained based on the resulting data of the viral test or the antibody test, as well as resulting data from executing the one or more illness risk factor assessment functions (see e.g. the above description associated with FIGS. 14-17). The access control data may then be derived, determined or retrieved based on the test result or score of the test.

Figure 19:
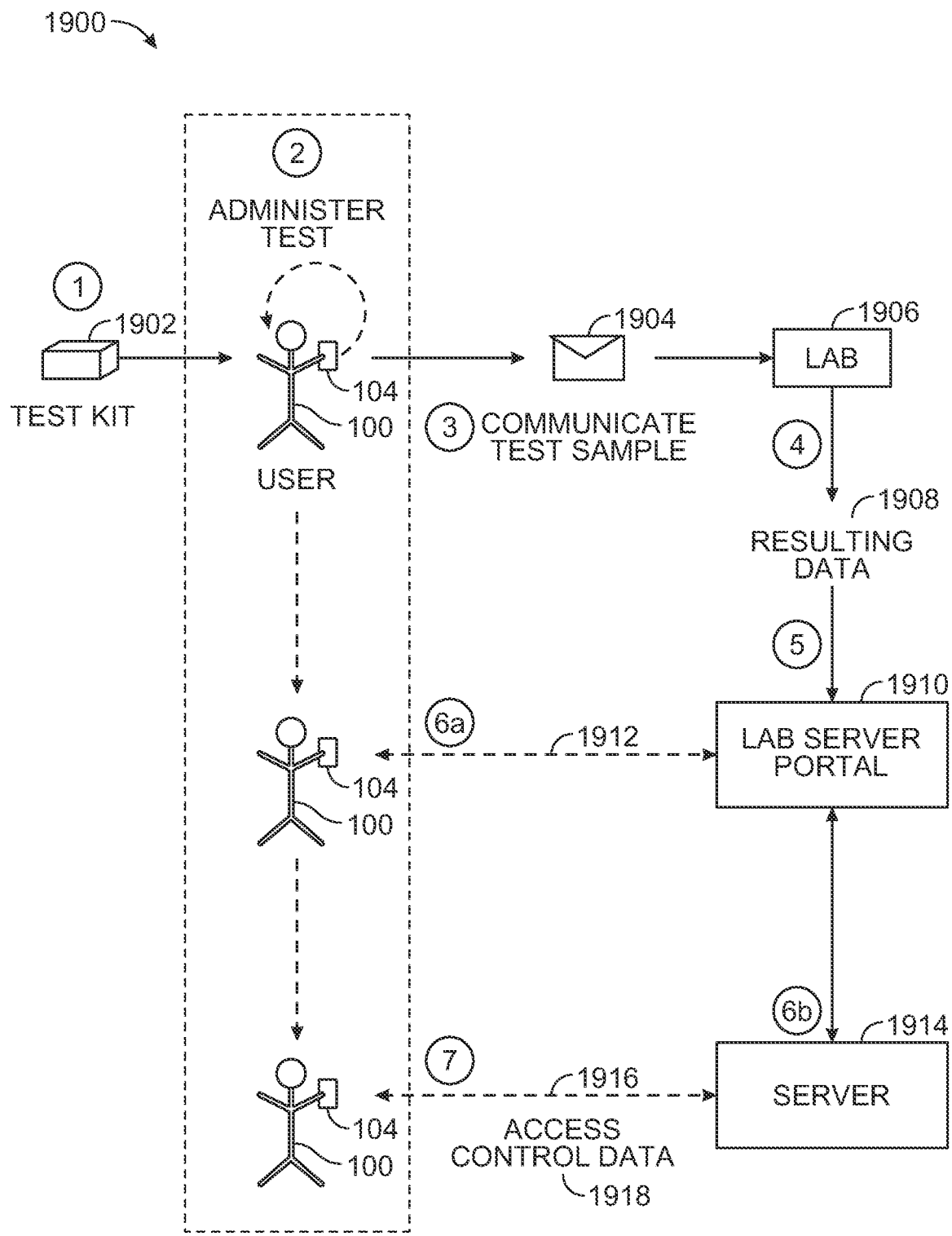
FIG. 19 is a process flow diagram of a process flow for obtaining a test result or score based on resulting data of a viral test or an antibody test obtained from a health care server portal by the mobile user device according to some embodiments.

FIG. 19 is a process flow diagram of a process flow 1900 for obtaining a test result or score based on resulting data of a viral test or an antibody test according to some embodiments. In this embodiment, process flow 1900 begins with a step 1. At step 1, a test for assessing a risk of a user of having or developing a contagious illness is obtained. In this example, the test is in the form of a test kit 1902 and, in particular, test kit 1902 may be an at-home test kit. The test may be for a viral test or an antibody test for the contagious illness. Next, process flow 1900 may proceed to a step 2, where the test is administered (e.g. at home or at employer) using the test kit to produce a test sample (e.g. a swab from the nose or the throat of the user, a blood sample of the user, etc.). Next, process flow 1900 may proceed to a step 3, where user 100 may then communicate or send the sample to a health care laboratory or "lab" 1906 via a package or mailing 1904. The viral test or the antibody test for the user may be processed at the health care laboratory 1906 based on the sample of user 100.

Next, process flow 1900 may proceed to a step 4, where resulting data 1908 of the viral test or the antibody test may be generated based on the sample. Next, process flow 1900 may proceed to a step 5, where the resulting data 1910 may be provided in the form of electronic data which is made privately available for viewing or retrieval via a health care server portal 1910 (or "lab server portal). Next, process flow 1900 may proceed to a step 6a, where user device 104 (e.g. a mobile user device) may retrieve or obtain the resulting data from the health care server portal 1910 in a communication 1912 (e.g. securely and privately via authentication). In some cases, the resulting data may be viewed at user device 104.

In some embodiments of step 6a of process flow 1900, user device 104 or its application may automatically retrieve or obtain the resulting data that is captured in the application (e.g. for providing access control). In some cases, user device 104 may retrieve the resulting data by regularly or periodically checking health care server portal 1910 for the resulting data. In other cases, health care server portal 1910 may send to user device 104 a notification in response to availability of the resulting data and, in response, user device 104 may then automatically retrieve or obtain the resulting data that is captured in the application.

In some embodiments of process flow 1900, after step 6a, user device 104 may derive or determine a user score based on the resulting data received from health care server portal 1910. The user score may be indicative of the risk of the user of having or developing the contagious illness. In one example of step 6a, the resulting data of the viral test or the antibody test is or includes the user score. In another example of step 6a, the user score may be obtained based on the resulting data of the viral test or the antibody test, as well as resulting data from executing the one or more illness risk factor assessment functions (see e.g. the above description associated with FIGS. 14-17).

In other embodiments of process flow 1900, after step 6a, alternative steps 6b and 7 may be carried out. Process flow 1900 may proceed to a step 6b, where a server 1914 (e.g. a trusted server) may retrieve or obtain the resulting data of user 100 from health care server portal 1910 (e.g. securely and privately via authentication). In an example embodiment, server 1914 may be a local server in a private LAN or WLAN of an organization that manages entry into an area. In another example embodiment, server 1914 may be an external server that is external to the private LAN or WLAN of the organization that manages entry. In some cases, server 1914 may be server 116 or server 172 described in relation to FIGS. 1-3.

In an example embodiment of step 6b of process flow 1900, server 1914 may automatically retrieve or obtain the resulting data associated with user 100. In some cases, server 1914 may retrieve the resulting data by regularly or periodically checking health care server portal 1910 for the resulting data. In another example embodiment of step 6*b* of process flow 1900, health care server portal 1910 may send to server 1914 a notification in response to availability of the resulting data and, in response, server 1914 may then automatically retrieve or obtain the resulting data.

Server 1914 may be configured to derive or determine the user score for user 100 (as well as other users) based on the resulting data. Next, process flow 1900 may proceed to step 7, where user device 104 (e.g. the mobile user device) may retrieve or obtain a user score 1918 from server 1914 in a communication 1916. In an example embodiment of step 7 of process flow 1900, user device 104 or its application may automatically retrieve or obtain user score 1918 that is captured in the application. Here, user device 104 may retrieve user score 1918 by regularly or periodically checking server 1914 for the resulting data. In another example embodiment of step 7 of process flow 1900, server 1914 may send to user device 104 a notification in response to availability of user score 1918 and, in response, user device 104 may then automatically retrieve or obtain user score 1918 that is captured in the application.

In some embodiments of step 7 of process flow 1900, user score 1918 from server 1914 may be provided in the form of QR code data for providing the user score. The QR code data may be for display in the display or touch screen display of user device 104 which may be a mobile user device. See e.g. QR code data 1215 of FIG. 12. The QR code data may be displayed for being read by a reader of an access control system (see e.g. FIGS. 1-3). Thus, the display or touch screen display of a mobile user device which displays the QR code data may be used for providing the user score of the user.

In additional or alternative embodiments, server 1914 may be configured to generate a group score based on a plurality of user scores for a plurality of users which include user 100. Server 1914 may obtain the plurality of user scores for the plurality of users in the same or similar manner as user 100. Again, in some cases, server 1914 may be server 116 shown and described in relation to FIGS. 1-3, which provides access to a group setting for the plurality of users. In other cases, server 1914 may be server 172 shown and described in relation to FIGS. 1-3, which may provide the communication of group scores associated with multiple group settings for display.

Figure 20:
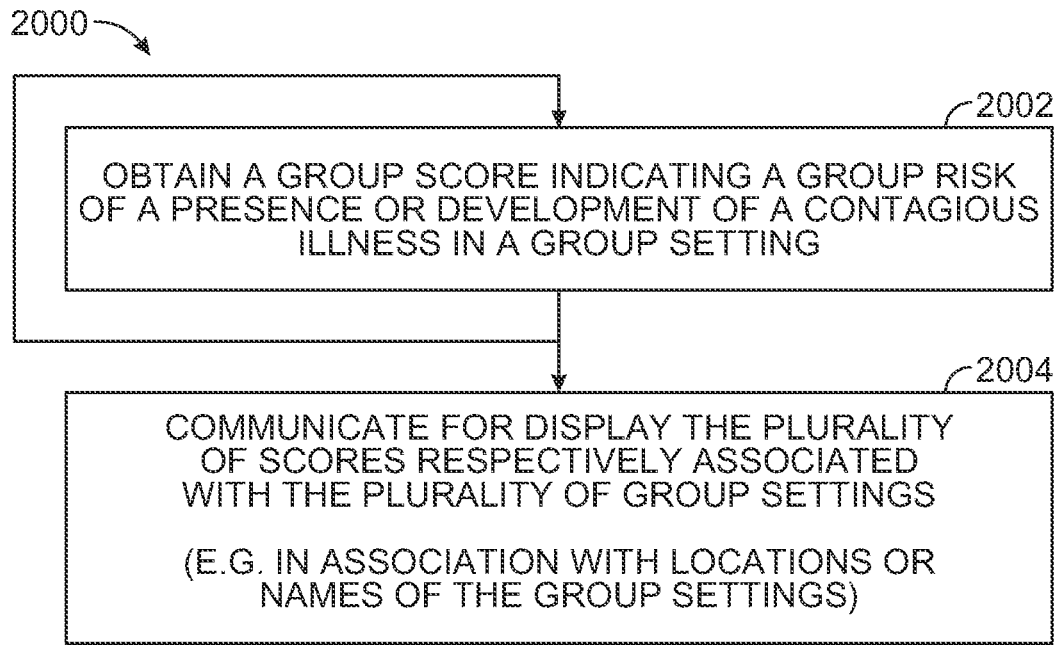
FIG. 20 is a flowchart for describing a method for use in accurately tracking and informing of health and safety for a plurality of group settings according to some embodiments, which may be performed by a server in communication with systems associated with the plurality of group settings, for example, with access control systems of the type shown and described in relation to FIGS. 1-3.

FIG. 20 is a flowchart for describing a method 2000 for use in accurately tracking and informing of health and safety for a plurality of group settings according to some embodiments. Method 2000 shown in FIG. 20 may be performed by a server (e.g. server 172 of FIG. 1) in communication with systems associated with the plurality of group settings, for example, with access control systems of the type shown and described in relation to FIGS. 1-3 (e.g. access control system 102 of FIGS. 1-3). Method 2000 may be embodied in a computer program product having a non-transitory computer readable medium and instructions stored in the non-transitory computer readable medium, where the instructions are executable by the server to perform steps of method 2000.

In the embodiment of FIG. 20, method 2000 begins with a step 2002. At step 2002, the server may obtain a score indicating a group risk of a presence or development of a contagious illness in a group setting. Next, method 2000 may proceed to repeat step 2002 for each next group setting of a plurality of group settings. Next, method 2000 may proceed to a step 2004, where the server may communicate for display the plurality of scores associated with the plurality of group settings. In some embodiments of method 2000, each score may be a group score which is obtained based on a plurality of user scores associated with a plurality of users in each group setting, where each user score may be obtained based on a reading of a user device of a user at an access control system used for entry into the group setting.

In an example embodiment of step 2004 of method 2000, the group score may be communicated for display by sending a message including the group score to a device having a display (see e.g. device 176 of FIG. 1). In another example embodiment of step 2004, the group score may be communicated for display by posting or publishing the group score in association with a location or name of the group setting on a website (see e.g. server 172 of FIG. 1).

In some embodiments of method 2000, the plurality of group settings may be identified by their locations or names. In example embodiments, at least a subset of the group settings may be grouped according to group setting type. Locations or names of the group settings of the grouped subset of the same group setting type may be communicated for display in association with their group scores.

Figure 21:
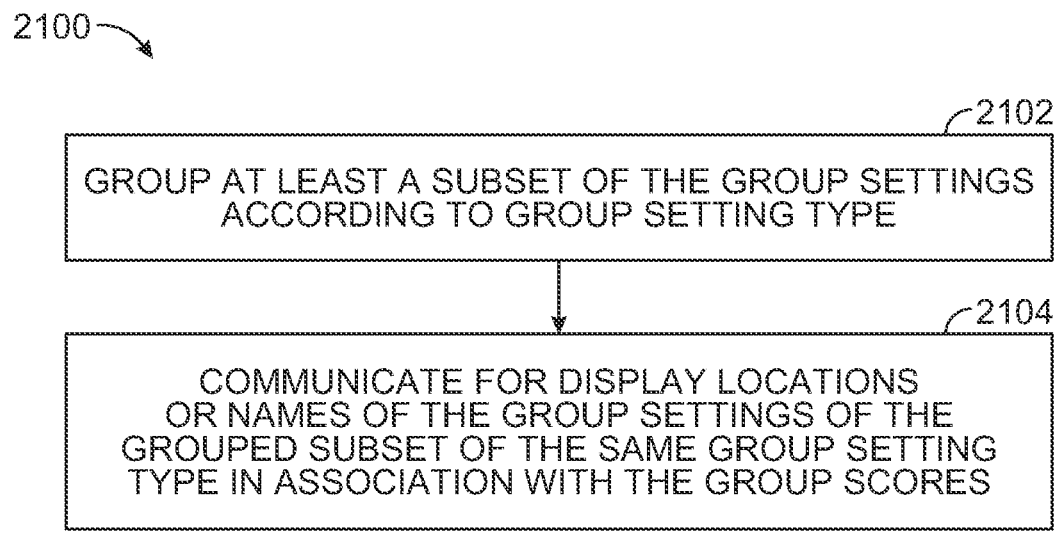
FIG. 21 is a flowchart for describing a method for use in accurately tracking and informing of health and safety for a plurality of group settings according to some embodiments, which may be performed by a server in communication with systems associated with the plurality of group settings and together with the method shown and described in relation to FIG. 20.

FIG. 21 is a flowchart for describing a method for use in accurately tracking and informing of health and safety for a plurality of group settings according to some embodiments. Method 2100 shown in FIG. 21 may be performed by a server (e.g. server 172 of FIG. 1) in communication with systems associated with the plurality of group settings, for example, with access control systems of the type shown and described in relation to FIGS. 1-3 (e.g. access control system 102 of FIGS. 1-3), and together with the method 2000 shown and described in relation to FIG. 20. In some embodiments of method 2100, the plurality of group settings may be identified by their locations or names.

In the embodiment of FIG. 21, method 2100 begins with a step 2102. At step 2102, the server may group at least a subset of group settings according to group setting type. As some examples, a first type of group setting may be a restaurant, a second type of group setting may be a coffee shop, a third type of group setting may be a hospital, a fourth type of group setting may be a park concert, etc. Next, method 2100 may proceed to a step 2104, where the server communicates for display the locations or the names of the group settings of the same group setting type along with their group scores.

FIG. 22 is an illustrative example of a display 2200 having a plurality of display items. The plurality of display items indicate a plurality of group scores 2304 respectively associated with a plurality of group settings 2202, which are displayed in grouped subsets of the same group subset type. Display 2200 of FIG. 22 is an illustrative example of displayed output from performing methods 2000 and 2100 shown and described in relation to FIGS. 20 and 21. In the example embodiment of FIG. 22, locations and names of the group settings 2202 for each grouped subset of each group setting type are displayed in association with their group scores 2204. As illustrated in FIG. 22, the first type of group setting is a restaurant (e.g. displaying names of RESTAURANT 1, 2, and 3), a second type of group setting is a coffee shop (e.g. displaying names of COFFEE SHOP 1, 2, and 3), a third type of group setting is a hospital (e.g. displaying names of HOSPITAL 1, 2, and 3), and a fourth type of group setting is a park concert (e.g. displaying names of PARK CONCERT 1, 2, and 3).

FIG. 23 is a flowchart for describing a method 2300 for use in accurately tracking and informing of health and safety for a plurality of group settings according to some embodiments. Method 2300 shown in FIG. 23 may be performed by a server (e.g. server 172 of FIG. 1) in communication with systems associated with the plurality of group settings, for example, with access control systems of the type shown and described in relation to FIGS. 1-3 (e.g. access control system 102 of FIGS. 1-3). Method 2300 shown in FIG. 23 may be performed by together with the methods 2000 and 2100 shown and described in relation to FIGS. 20 and 21.

In the embodiment of method 2300, a plurality of group scores of a plurality of group settings are stored in association with a plurality of locations. The plurality of locations may be or be provided as geographic positions or coordinates (e.g. latitude and longitude data).

Figure 24:
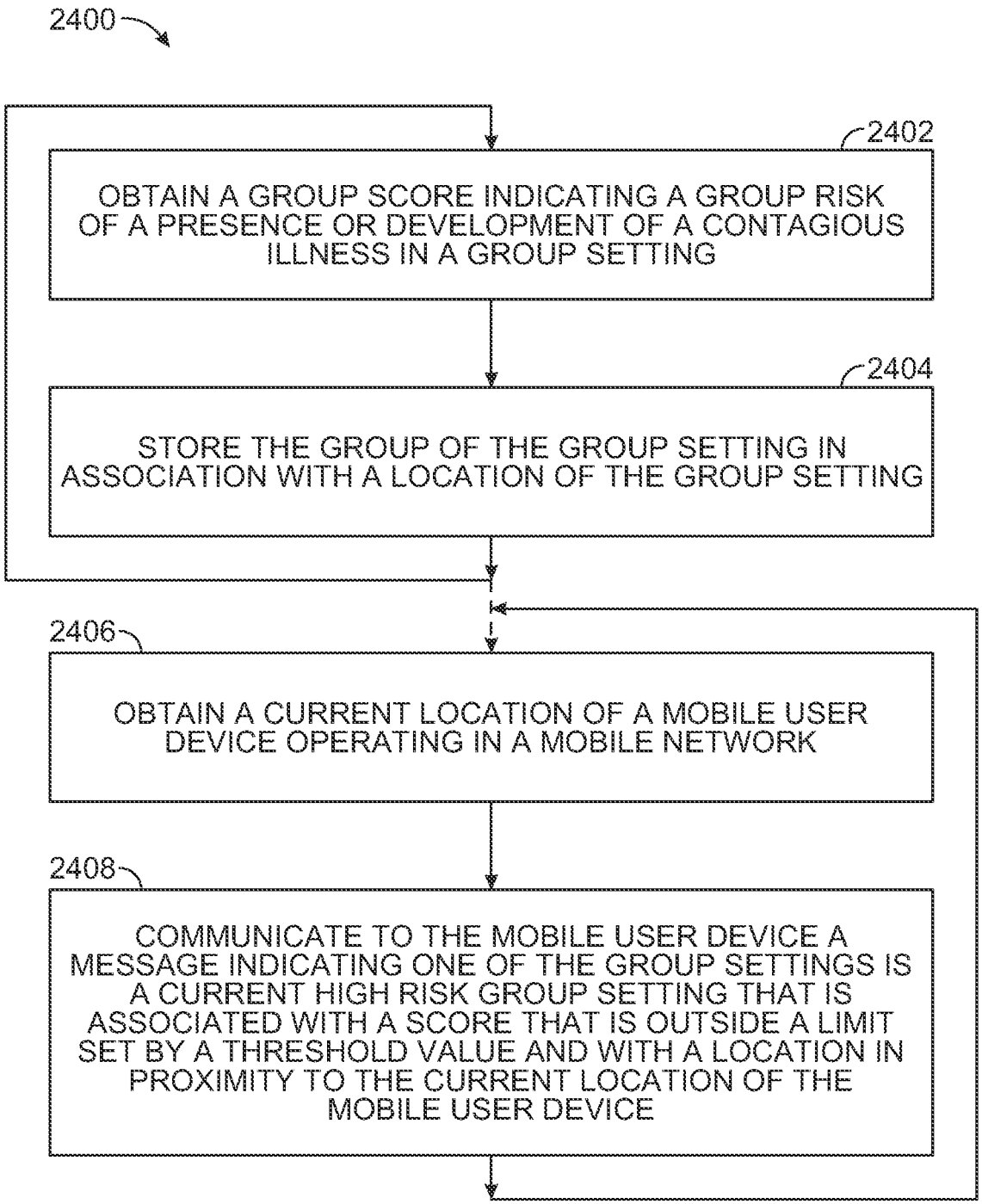
FIG. 24 is a flowchart for describing a location-based method for use in accurately tracking and informing of health and safety for group settings according to some embodiments, which may be performed by a server in communication with systems associated with the plurality of group settings, for informing or alerting a mobile user device of a user of a current high risk group setting associated with a location in proximity to a current location of the mobile user device.

In the embodiment of FIG. 23, method 2300 begins with a step 2302. At step 2302, the server may provide the plurality of group scores associated with the plurality of locations on an interactive map of a web mapping service and application. The group scores or indications thereof may be added to the interactive map through a selected one of a plurality of APIs (Application Programming Interfaces) and/or utilities for the web mapping service. In one example, the group scores may be associated with graded heatmap colors of a heatmap for visualizing the intensity of the data at geographical points. With this arrangement, a user device or mobile user device may be FIG. 24 is a flowchart for describing a location-based method 2400 for use in accurately tracking and informing of health and safety for group settings for a mobile user device according to some embodiments. Method 2400 shown in FIG. 24 may be performed by a server (e.g. server 172 of FIG. 1) in communication with systems associated with the plurality of group settings, for example, with access control systems of the type shown and described in relation to FIGS. 1-3 (e.g. access control system 102 of FIGS. 1-3). Method 2400 may be embodied in a computer program product having a non-transitory computer readable medium and instructions stored in the non-transitory computer readable medium, where the instructions are executable by the server to perform steps of method 2000.

In the embodiment of FIG. 24, method 2400 begins with a step 2402. At step 2402, the server may obtain a score indicating a group risk of a presence or development of a contagious illness in a group setting. In some embodiments of step 2402, each score may be a group score which is obtained based on a plurality of user scores associated with a plurality of users in each group setting, where each user score may be obtained based on a reading of a user device of a user at an access control system used for entry into the group setting. Next, method 2400 may proceed to a step 2404, where the server may store the score of the group setting in association with a location of the group setting. Next, method 2400 may proceed to repeat steps 2402 and 2404 for each next group setting of a plurality of group settings.

Next, method 2400 may proceed to a step 2406, where the server may obtain a current location of a mobile user device connected in a mobile network for communications. In some embodiments of step 2406, the server may obtain the current location of the mobile user device using LBS (location-based services) of the mobile network (see e.g. LBS 1290 of FIG. 13). In example embodiments of step 2406, the server may obtain the current location of the mobile user device from the mobile user device. Next, method 2400 may proceed to a step 2408, where the server may communicate to the mobile user device a message indicating or alerting one of the plurality of group settings as a current high risk group setting that is associated with a score that is outside a limit set by a threshold value and with a location in proximity to the current location of the mobile user device.

In some embodiments of steps 2406 and 2408, the server may regularly monitor the (e.g. changing) current location of mobile user device and compare it to one or more locations of one or more group settings associated with group scores that are outside of the limit set by the threshold value. In response to or based on identifying a match between the locations, the server may communicate the message indicating or alerting of the current high risk group setting. In example embodiments, the indicating or alerting at the mobile user device may be provided in the form of a message indication, a visual alert or flashing, an audible alert, a vibrating alert, or the like.

In some embodiments of method 2400, the threshold value may be user-settable by the user of the mobile user device. In response to a setting or selecting of the threshold value, the mobile user device may send a message to the server via the mobile network. The server may use the newly set or selected threshold value for comparative purposes during its monitoring.

Figure 25:
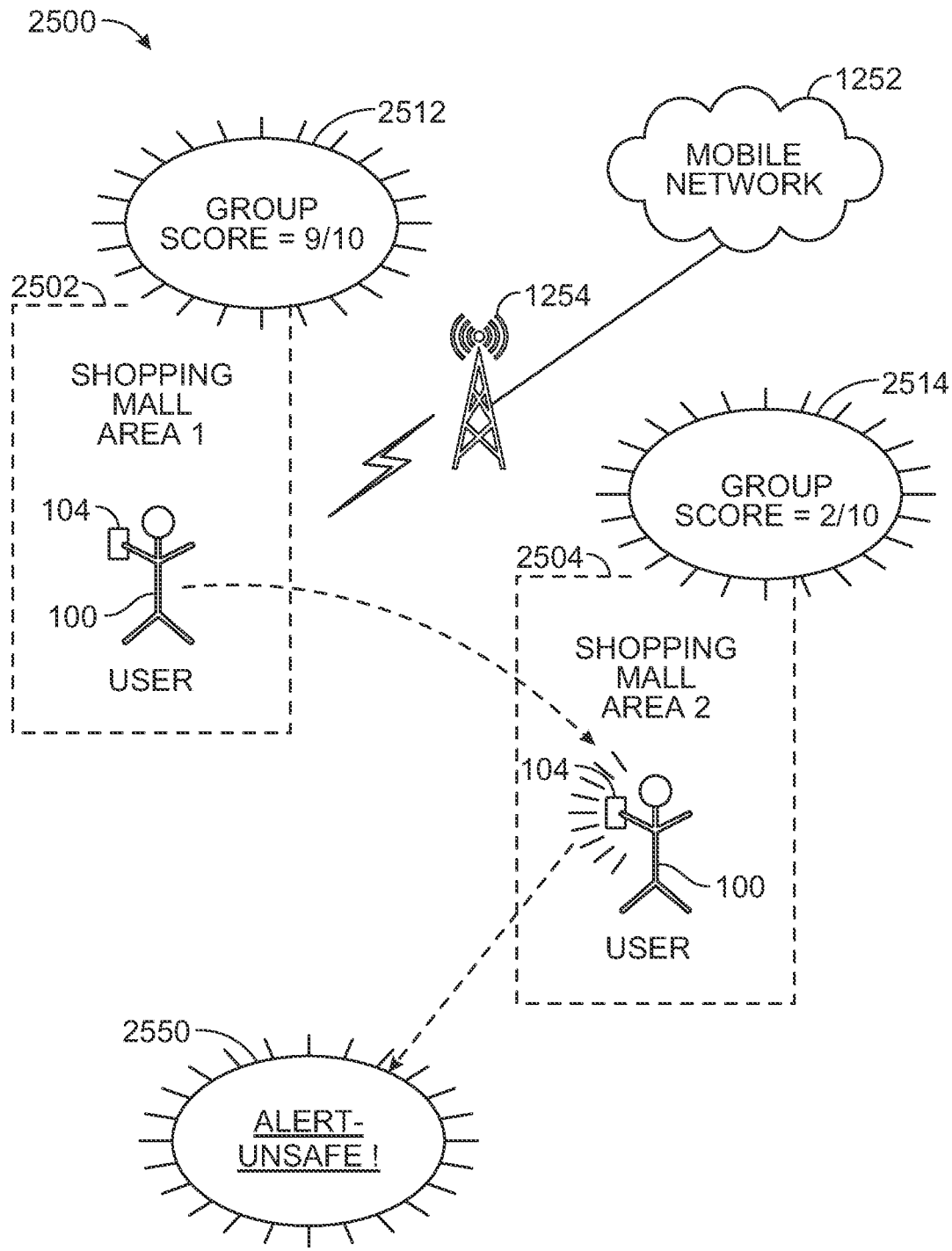
FIG. 25 is an illustrative scenario of the mobile user device of the user being informed or alerted of the current high risk group setting associated with the location in proximity to the current location of the mobile user device according to the location-based method shown and described in relation to FIG. 24.

FIG. 25 is an illustrative scenario 2500 of user device 104 of user 100 being informed or alerted of a current high risk group setting according to method 2400 shown in FIG. 24. To begin in FIG. 25, user 100 having user device 104 is located at a first location associated with a group setting 2502. Group setting 2502 corresponds to SHOPPING MALL 1 associated with a group score 2512 which is 9 out of 10 (9/10). Group score 2512 is indicative of a low risk of the presence or development of the contagious illness in group setting 2502. Next, user 100 having user device 104 moves to a second location associated with a group setting 2504. Group setting 2504 corresponds to SHOPPING MALL 2 associated with a group score 2514 which is 2 out of 10 (2/10). Group score 2514 is indicative of a high risk of the presence or development of the contagious illness in group setting 2504. The server may obtain the current location of user device 104 and identify that group setting 2504 is associated with a location in proximity to the current location. As group score 2514 of group setting 2504 is detected to be outside the limit set by the threshold value, the server communicates to user device 104 via the mobile network 1252 a message indicating or alerting group setting 2504 to be a current high risk group. An indication or alert 2550 is provided at user device 104 of user 100.

Accordingly, techniques and mechanisms of the present disclosure may provide reasonable measures to prevent the spread of disease in operating environments (e.g. employment environments) by the informing of group scores indicating group risks of the presence or development of the disease in group settings. Assurance of health and safety in group settings are easily facilitated, leveraging existing technology where possible to minimize changes to existing devices, systems, and network architectures. By removing any actual test results or user scores of the tests of the users upon generation of the group scores, compliance with HIPAA and/or other regulatory standards, policies, and practices may be established. Use of sensitive test results or user scores of users in the network or system may be immediately discarded (e.g. deleted or cleared) after derivation of the group scores.

The processes and methods of the embodiments described in this detailed description and shown in the figures can be implemented using any kind of servers or devices having one or more central processing units (CPUs) and/or graphics processing units (GPUs). The processes and methods of the embodiments could also be implemented using special purpose circuitry such as an application specific integrated circuit (ASIC). The processes and methods of the embodiments may also be implemented on servers or devices including read only memory (ROM) and/or random access memory (RAM), which may be connected to one or more processing units. Examples of servers and devices include, but are not limited to: enterprise servers, cloud servers, cellular phones, smart phones, tablet computers, notebook computers, e-book readers, laptop or desktop computers, all-in-one computers, as well as various kinds of digital media players.

The processes and methods of the embodiments can be stored as instructions and/or data on non-transitory computer-readable media. Examples of media that can be used for storage include erasable programmable read-only memory (EPROM), electrically erasable programmable read-only memories (EEPROM), solid state drives, magnetic disks or tapes, optical disks, CD ROM disks and DVD-ROM disks.

The embodiments may utilize any kind of network for communication between separate computing systems. A network can comprise any combination of LANs and/or WANs, using both wired and wireless communication systems. A network may use various known communications technologies and/or protocols. Communication technologies can include, but are not limited to: Ethernet, 802.11, worldwide interoperability for microwave access (WiMAX), mobile broadband (such as CDMA, and LTE), digital subscriber line (DSL), cable internet access, satellite broadband, wireless ISP, fiber optic internet, as well as other wired and wireless technologies. Networking protocols used on a network may include transmission control protocol/Internet protocol (TCP/IP), multiprotocol label switching (MPLS), User Datagram Protocol (UDP), hypertext transport protocol (HTTP) and file transfer protocol (FTP) as well as other protocols.

Data exchanged over a network may be represented using technologies and/or formats including hypertext markup language (HTML), extensible markup language (XML), Atom, JavaScript Object Notation (JSON), YAML, as well as other data exchange formats. In addition, information transferred over a network can be encrypted using conventional encryption technologies such as secure sockets layer (SSL), transport layer security (TLS), and Internet Protocol security (IPsec).

For each of the exemplary processes described above including multiple steps, it may be understood that other embodiments some steps may be omitted and/or reordered. In some other embodiments, additional steps could also be possible.

While various embodiments of the invention have been described, the description is intended to be exemplary, rather than limiting, and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

The invention claimed is:

1. A method comprising:
   providing a plurality of access control systems, each access control system being associated with a group setting of a plurality of group settings, wherein the access control system is operative to permit entry to the group setting to one or more users of a plurality of users;
   providing a first server associated with each access control system, the first server managing entry into the respective group setting for the one or more users of the plurality of users;
   providing a second server in communication with the first server associated with each access control system for the group setting of the plurality of group settings, the second server:
      obtaining a score indicating a group risk of a presence or development of a contagious illness in the group setting, for each group setting of the plurality of group settings; and
      communicating for display the scores associated with the plurality of group settings;
   wherein the first server is configured to permit or deny entry to the respective group setting to each of the one or more users based on a user score reading obtained by the access control system from a mobile user device of the user by communicating a signal to an entry mechanism of the access control system to open or close the entry mechanism;
   wherein the score associated with the group setting is stored in association with a location of the group setting, for each group setting of the plurality of group settings, the method further comprising:
   at the server,
      monitoring a current location of a mobile user device of the one or more users of the plurality of users operating in a mobile network;
      comparing the current location of the mobile user device to one or more locations of the plurality of group settings;
      upon identifying a match between the current location and the one or more locations of the plurality of group settings, communicating to the mobile user device a message indicating at least one group setting of the plurality of group settings as a current high risk group setting that is associated with a score that is outside a limit set by a threshold value and with a location in proximity to the current location of the mobile user device; and
      wherein the threshold value for the score associated with the group setting is set by the user of the mobile user device.

2. The method of claim 1, wherein the score comprises a group score which is obtained based on a plurality of user scores associated with the plurality of users in the group setting.

3. The method of claim 2, further comprising:
   at the server,
      for each exiting user of a plurality of exiting users that leaves the group setting, updating the group score based on remaining user scores of a remaining plurality of users in the group setting.

4. The method of claim 2, wherein communicating for display the scores comprises at least one of:
   communicating for display the group score in a display of the group setting;
   sending a message including the group score to a device having a display; or
   posting or publishing the group score in association with a location or name of the group setting on a website.

5. The method of claim 2, wherein each user score is based on a reading of a user device of a user of the plurality of users at an access control system of the plurality of access control systems for entry in the group setting.

6. The method of claim 5, wherein each user score is from a test for assessing a risk of a user of having or developing the contagious illness.

7. The method of claim 1, wherein:
the group setting is associated with a building space having a building space location area;
the group setting s associated with an outdoor venue having an outdoor venue location area; or
the group setting is associated with a plurality of building spaces at different building space location areas and managed by the same organization having an organization name.

8. The method of claim 1, further comprising:
at the server,
grouping at least a subset of the group settings according to a group setting type,
wherein communicating for display the scores further comprises communicating for display locations or names of the group settings of the grouped subset of the same group setting type in association with the scores.

9. The method of claim 1, wherein obtaining the user score is from a test for assessing a risk of the user having or developing a contagious illness that is based on resulting data from executing an illness risk factor assessment function on the mobile user device which comprises the test, wherein the illness risk factor assessment function is an image-based symptom recognition function which is based on facial characteristics of the user obtained through a camera of the mobile user device.

10. The method of claim 9, wherein at least one additional illness risk factor assessment function comprises one or more of:
a temperature reading function which is based on a temperature of the user;
an audio-based symptom recognition function which is based on qualities of voice, nasal, or congestion of the user, using an audio recorder of the mobile user device; or
a pulse oximeter function which is based on a blood oxygenation of the user.

11. A system comprising:
a plurality of access control systems, each access control system being associated with a group setting of a plurality of group settings, wherein the access control system is operative to permit entry to the group setting to one or more users of a plurality of users;
a first server associated with each access control system, the first server managing entry into the respective group setting for the one or more users of the plurality of users, the first server configured to connect in a network;
a second server in communication with the first server associated with each access control system for the group setting of the plurality of group settings, the second server configured to connect in the network;
a mobile user device associated with a user of the plurality of users, the mobile user device configured to connect in a mobile network for communications;
the second server being configured to:
obtain a score indicating a group risk of a presence or development of a contagious illness in the group setting and store the score in association with a location of the group setting, for each group setting of the plurality of group settings;
monitor a current location of the mobile user device connected in the mobile network;
compare the current location of the mobile user device to one or more locations of the plurality of group settings;
upon identifying a match between the current location and the one or more locations of the plurality of group settings, communicate to the mobile user device a message indicating at least one group setting of the plurality of group settings as a current high risk group setting that is associated with a score that is outside a limit set by a threshold value and with a location in proximity to the current location of the mobile user device, wherein the threshold value for the score associated with the group setting is set by the user of the mobile user device;
wherein the first server is configured to permit or deny entry to the respective group setting to each of the one or more users based on a user score reading obtained by the access control system from the mobile user device of the user by communicating a signal to an entry mechanism of the access control system to open or close the entry mechanism.

12. The system of claim 11, wherein the message is communicated for alerting the mobile user device of the high risk group setting.

13. The system of claim 11, wherein the message comprises at least one of a visual alert, an audible alert, or a vibrating alert.

14. The system of claim 11, wherein obtaining the user score is from a test for assessing a risk of the user having or developing a contagious illness that is based on resulting data from executing an illness risk factor assessment function on the mobile user device which comprises the test, wherein the illness risk factor assessment function is an image-based symptom recognition function which is based on facial characteristics of the user obtained through a camera of the mobile user device.

* * * * *